(12) United States Patent
Utsumi et al.

(10) Patent No.: US 8,519,073 B2
(45) Date of Patent: *Aug. 27, 2013

(54) COMPOUND AND POLYMERIC COMPOUND

(75) Inventors: Yoshiyuki Utsumi, Kawasaki (JP); Hiroaki Shimizu, Kawasaki (JP); Kyoko Ohshita, Kawasaki (JP); Toshiharu Shimamaki, Osaka (JP); Kenshin Niwa, Osaka (JP); Seihin Shu, Osaka (JP)

(73) Assignees: Tokyo Ohka Kogyo Co., Ltd., Kawasaki-shi (JP); Daito Chemix Corporation, Osaka (JP)

( * ) Notice: Subject to any disclaimer, the term of this patent is extended or adjusted under 35 U.S.C. 154(b) by 459 days.

This patent is subject to a terminal disclaimer.

(21) Appl. No.: 12/447,433

(22) PCT Filed: Oct. 15, 2007

(86) PCT No.: PCT/JP2007/070103
§ 371 (c)(1),
(2), (4) Date: Apr. 27, 2009

(87) PCT Pub. No.: WO2008/053698
PCT Pub. Date: May 8, 2008

(65) Prior Publication Data
US 2010/0069590 A1 Mar. 18, 2010

(30) Foreign Application Priority Data
Oct. 31, 2006 (JP) .................. 2006-296893

(51) Int. Cl.
*C08F 18/20* (2006.01)

(52) U.S. Cl.
USPC ..... 526/245; 526/281; 526/292.1; 526/292.7; 526/309; 430/270.1; 560/219; 560/223; 560/227; 560/229

(58) Field of Classification Search
USPC .................. 526/245; 560/229, 219, 227, 228, 560/223
See application file for complete search history.

(56) References Cited

U.S. PATENT DOCUMENTS
3,457,247 A * 7/1969 Fukui et al. .................. 526/245
(Continued)

FOREIGN PATENT DOCUMENTS
JP A-09-043848 2/1997
(Continued)

OTHER PUBLICATIONS
Machine translation of Koyama et al., JP 2005-008756 A, retrieved Aug. 30, 2011.*
(Continued)

*Primary Examiner* — Nicole M Buie-Hatcher
(74) *Attorney, Agent, or Firm* — Knobbe Martens Olson & Bear LLP

(57) ABSTRACT

A compound represented by general formula (I); and a polymeric compound including a structural unit (a1) represented by general formula (II).

[Chemical Formula 1]

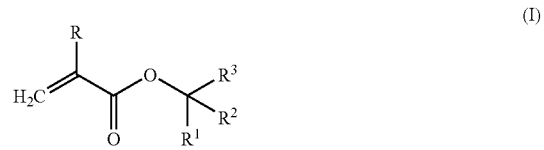

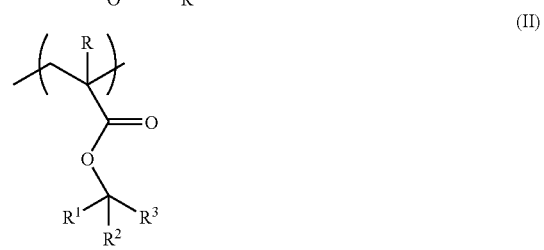

wherein R represents a hydrogen atom, a halogen atom, a lower alkyl group or a halogenated lower alkyl group; each of $R^1$ to $R^3$ independently represents an alkyl group or a fluorinated alkyl group, with the provision that no fluorine atom is bonded to a carbon atom adjacent to the tertiary carbon atom to which $R^1$ to $R^3$ are bonded, and at least one of $R^1$ to $R^3$ represents a fluorinated alkyl group; and $R^2$ and $R^3$ may form a ring structure.

7 Claims, 2 Drawing Sheets

(56) References Cited

U.S. PATENT DOCUMENTS

| | | | |
|---|---|---|---|
| 4,500,694 A * | 2/1985 | Ohmori et al. | 526/245 |
| 5,945,517 A | 8/1999 | Nitta et al. | |
| 6,153,733 A | 11/2000 | Yukawa et al. | |
| 6,683,202 B2 * | 1/2004 | Ogata et al. | 560/129 |
| 6,723,485 B1 | 4/2004 | Ootani et al. | |
| 6,878,502 B2 * | 4/2005 | Mizutani et al. | 430/270.1 |
| 8,105,747 B2 * | 1/2012 | Utsumi et al. | 430/270.1 |
| 2001/0033989 A1 | 10/2001 | Harada et al. | |
| 2001/0049075 A1 | 12/2001 | Kishimura et al. | |
| 2003/0078352 A1 | 4/2003 | Miyazawa et al. | |
| 2003/0134224 A1 | 7/2003 | Mizutani et al. | |
| 2004/0236046 A1 | 11/2004 | Miyazawa et al. | |
| 2006/0057489 A1 * | 3/2006 | Sumida et al. | 430/270.1 |
| 2006/0063102 A1 | 3/2006 | Kubota et al. | |
| 2006/0105269 A1 * | 5/2006 | Khojasteh et al. | 430/270.1 |
| 2006/0217507 A1 | 9/2006 | Miyazawa et al. | |
| 2006/0252897 A1 | 11/2006 | Miyazawa et al. | |
| 2007/0099114 A1 | 5/2007 | Watanabe et al. | |
| 2007/0231738 A1 | 10/2007 | Kaneko et al. | |
| 2007/0231741 A1 | 10/2007 | Nishi et al. | |
| 2008/0081290 A1 | 4/2008 | Wada et al. | |
| 2009/0048409 A1 | 2/2009 | Endo et al. | |
| 2010/0069590 A1 | 3/2010 | Utsumi et al. | |

FOREIGN PATENT DOCUMENTS

| | | |
|---|---|---|
| JP | H09-208554 | 8/1997 |
| JP | H11-035551 | 2/1999 |
| JP | H11-035552 | 2/1999 |
| JP | H11-035573 | 2/1999 |
| JP | H11-322707 | 11/1999 |
| JP | A-2000-321774 | 11/2000 |
| JP | A-2001-154362 | 6/2001 |
| JP | A-2001-302726 | 10/2001 |
| JP | A-2002-006501 | 1/2002 |
| JP | 2002-220420 | 8/2002 |
| JP | 2003-015298 | 1/2003 |
| JP | A-2003-015297 | 1/2003 |
| JP | 2003-040840 | 2/2003 |
| JP | 2003-322972 | 11/2003 |
| JP | A-2004-233953 | 8/2004 |
| JP | A-2004-361629 | 12/2004 |
| JP | 2005008756 A * | 1/2005 |
| JP | 2005-029539 | 2/2005 |
| JP | A-2006-243264 | 9/2006 |
| JP | A-2006-349800 | 12/2006 |
| JP | 2007-119678 | 5/2007 |
| JP | A-2007-155991 | 6/2007 |
| JP | A-2007-233322 | 9/2007 |
| JP | A-2007-297590 | 11/2007 |
| JP | A-2008-107806 | 5/2008 |
| TW | 200634435 | 10/2006 |
| WO | WO 2004-074242 | 9/2004 |
| WO | WO 2008/053698 | 5/2008 |

OTHER PUBLICATIONS

International Search Report issued for corresponding PCT Application No. PCT/JP2007/070103, dated Dec. 4, 2007.

D. Gil et al., "First Microprocessors with Immersion Lithography," Optical Microlithography XVIII, Proceedings of SPIE (U.S.), vol. 5754, pp. 119-128 (2005).

Shun-Ichi Kodama et al., "Synthesis of Novel Fluoropolymer for 157nm Photoresists by Cyclo-polymerization." Advances in Resist Technology and Processing XIX, Proceedings of SPIE (U.S.), vol. 4690 (2002), pp. 76-83.

International Search Report issued for corresponding PCT Application No. PCT/JP2007/070102, dated Nov. 27, 2007.

* cited by examiner

COMPOUND AND POLYMERIC COMPOUND

RELATED APPLICATIONS

This application is the U.S. National Phase filing under 35 U.S.C. §371 of PCT/JP2007/070103, filed Oct. 15, 2007, which designated the United States and was published in a language other than English, which claims priority under 35 U.S.C. §119(a)-(d) to Japanese Patent Application No. 2006-296893, filed Oct. 31, 2006. The contents of these applications are incorporated herein by reference in their entireties.

TECHNICAL FIELD

The present invention relates to a novel compound, and a polymeric compound including the compound as a monomer unit, which can be preferably used as a component of a positive resist composition.

BACKGROUND ART

In lithography techniques, for example, a resist film composed of a resist material is formed on a substrate, and the resist film is subjected to selective exposure of radial rays such as light or an electron beam through a mask having a predetermined pattern, followed by development, thereby forming a resist pattern having a predetermined shape on the resist film.

For miniaturization of semiconductor devices, technologies which shorten the wavelength of the exposure light source, and increase the numerical aperture (NA) of the projector lens have progressed. Currently, exposure apparatuses in which an ArF excimer laser having a wavelength of 193 nm is used as an exposure light source and NA=0.84 have been developed. As shortening the wavelength of the exposure light source progresses, it is required to improve various lithography properties of the resist material, such as the sensitivity to the exposure light source and a resolution capable of reproducing patterns of minute dimensions. As a resist material which satisfies these conditions, a chemically amplified resist is used, which includes a base resin that exhibits a changed alkali solubility under action of acid and an acid generator that generates acid upon exposure.

Currently, resins that contain structural units derived from (meth)acrylate esters within the main chain (acrylic resins) are now widely used as base resins for resists that use ArF excimer laser lithography, as they exhibit excellent transparency in the vicinity of 193 nm. Here, the term "(meth)acrylic acid" is a generic term that includes either or both of acrylic acid having a hydrogen atom bonded to the α-position and methacrylic acid having a methyl group bonded to the α-position. The term "(meth)acrylate ester" is a generic term that includes either or both of the acrylate ester having a hydrogen atom bonded to the α-position and the methacrylate ester having a methyl group bonded to the α-position.

The term "(meth)acrylate" is a generic term that includes either or both of the acrylate having a hydrogen atom bonded to the α-position and the methacrylate having a methyl group bonded to the α-position.

As a technique for further improving the resolution, a lithography method called liquid immersion lithography (hereafter, frequently referred to as "immersion exposure") is known in which exposure (immersion exposure) is conducted in a state where the region between the lens and the resist layer formed on a wafer is filled with a solvent (a immersion medium) that has a larger refractive index than the refractive index of air (see for example, Non-Patent Document 1).

According to this type of immersion exposure, it is considered that higher resolutions equivalent to those obtained using a shorter wavelength light source or a larger NA lens can be obtained using the same exposure light source wavelength, with no lowering of the depth of focus. Furthermore, immersion exposure can be conducted using a conventional exposure apparatus. As a result, it is expected that immersion exposure will enable the formation of resist patterns of higher resolution and superior depth of focus at lower costs. Accordingly, in the production of semiconductor devices, which requires enormous capital investment, immersion exposure is attracting considerable attention as a method that offers significant potential to the semiconductor industry, both in terms of cost and in terms of lithography properties such as resolution.

Immersion lithography is effective in forming patterns having various shapes. Further, immersion exposure is expected to be capable of being used in combination with currently studied super-resolution techniques, such as a phase shift method and a modified illumination method. Currently, as the immersion exposure technique, a technique using an ArF excimer laser as an exposure source is being actively studied, and water is mainly used as the immersion medium.

In recent years, fluorine-containing compounds have been attracting attention for their properties such as water repellency and transparency, and active research and development of fluorine-containing compounds have been conducted in various fields. For example, in the field of resist materials, currently, an acid-labile group such as a methoxyethyl group, tert-butyl group or tert-butoxycarbonyl group is being introduced into a fluorine-containing polymeric compound, and the fluorine-containing polymeric compound is used as a base resin for a chemically amplified positive resist. However, when such a fluorine-containing polymeric compound is used as a base resin for a chemically amplified positive resist, disadvantages are caused in that a large amount of an out gas is generated, and resistance to a dry-etching gas (etching resistance) is unsatisfactory.

Recently, as a fluorine-containing polymeric compound exhibiting excellent etching resistance, a fluorine-containing polymeric compound having an acid-labile group containing a cyclic hydrocarbon group has been reported (see, for example, Non-Patent Document 2).

[Non-Patent Document 1] Proceedings of SPIE, vol. 5754, pp. 119-128 (2005)

[Non-Patent Document 2] Proceedings of SPIE—The International Society for Optical Engineering (2002), vol. 4690, pp. 76-83

DISCLOSURE OF INVENTION

Problems to be Solved by the Invention

In immersion exposure, it is required to use a resist material which exhibits not only general lithography properties (e.g., sensitivity, resolution, etching resistance and the like), but also properties suited for immersion lithography. For example, when the immersion medium is water, and immersion exposure is performed using a scanning-type immersion exposure apparatus as disclosed in Non-Patent Document 1, tracking ability of water with respect to the movement of the lens (hereafter, frequently referred to as "water tracking ability") is required. When the water tracking ability is low, the exposure speed becomes low, and as a result, there is a possibility that the productivity is adversely affected. It is presumed that the water tracking ability can be improved by enhancing the hydrophobicity of the resist film (rendering the resist film hydrophobic). However, when the resist film is simply rendered hydrophobic, lithography properties are adversely affected, e.g., resolution and sensitivity is deteriorated, and the amount of scum generated tends to increase.

Thus, in immersion lithography, development of a material that exhibits an appropriate hydrophobicity becomes an important task.

However, at present, a material exhibiting both of excellent lithography properties and properties required for immersion lithography is essentially unknown.

The present invention takes the above circumstances into consideration, with an object of providing a novel compound, and a polymeric compound including the compound as a monomer unit, which can be preferably used as a component of a positive resist composition.

Means to Solve the Problems

A first aspect of the present invention for solving the above-mentioned problems is a compound represented by general formula (I) shown below:

[Chemical Formula 1.]

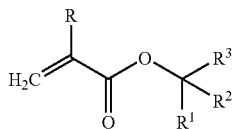

(I)

wherein R represents a hydrogen atom, a halogen atom, a lower alkyl group or a halogenated lower alkyl group; each of $R^1$ to $R^3$ independently represents an alkyl group or a fluorinated alkyl group, with the provision that no fluorine atom is bonded to a carbon atom adjacent to the tertiary carbon atom to which $R^1$ to $R^3$ are bonded, and at least one of $R^1$ to $R^3$ represents a fluorinated alkyl group; and $R^2$ and $R^3$ may form a ring structure.

Further, a second aspect of the present invention is a polymeric compound comprising a structural unit (a1) represented by general formula (II) shown below:

[Chemical Formula 2.]

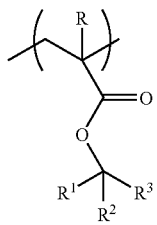

(II)

wherein R represents a hydrogen atom, a halogen atom, a lower alkyl group or a halogenated lower alkyl group; each of $R^1$ to $R^3$ independently represents an alkyl group or a fluorinated alkyl group, with the provision that no fluorine atom is bonded to a carbon atom adjacent to the tertiary carbon atom to which $R^1$ to $R^3$ are bonded, and at least one of $R^1$ to $R^3$ represents a fluorinated alkyl group; and $R^2$ and $R^3$ may form a ring structure.

In the present description and claims, an "alkyl group" includes linear, branched or cyclic, monovalent saturated hydrocarbon, unless otherwise specified.

A "lower alkyl group" is an alkyl group of 1 to 5 carbon atoms.

The term "alkylene group" includes linear, branched or cyclic divalent saturated hydrocarbon, unless otherwise specified.

The term "structural unit" refers to a monomer unit that contributes to the formation of a resin component (polymer or copolymer).

The term "exposure" is used as a general concept that includes irradiation with any form of radiation.

Effect of the Invention

According to the present invention, there are provided a novel compound, and a polymeric compound including the compound as a monomer unit, which can be preferably used as a component of a positive resist composition.

BEST MODE FOR CARRYING OUT THE INVENTION

Compound

Figure 1:
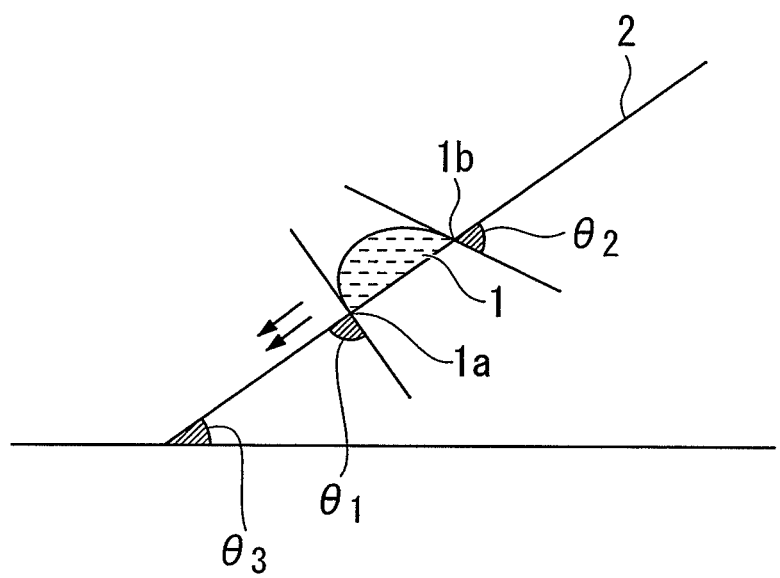
FIG. 1 is an explanatory diagram of an advancing angle ($\theta_1$), a receding angle ($\theta_2$) and a sliding angle ($\theta_3$).

The compound of the present invention (hereafter, referred to as "compound (I)") is represented by general formula (I) above.

In general formula (I), R represents a hydrogen atom, a halogen atom, a lower alkyl group or a halogenated lower alkyl group.

Examples of halogen atoms include a fluorine atom, a chlorine atom, a bromine atom and an iodine atom, and a fluorine atom is particularly desirable.

Specific examples of lower alkyl groups include linear or branched lower alkyl groups such as a methyl group, an ethyl group, a propyl group, an isopropyl group, an n-butyl group, an isobutyl group, a tert-butyl group, a pentyl group, an isopentyl group, and a neopentyl group.

Examples of halogenated lower alkyl groups include groups in which a part or all of the hydrogen atoms of the aforementioned lower alkyl group is substituted with the aforementioned halogen atoms.

Among these examples, a hydrogen atom, a fluorine atom, a lower alkyl group or a fluorinated lower alkyl group is preferable, and a hydrogen atom or a methyl group is particularly desirable in terms of industrial availability.

In general formula (I), each of $R^1$ to $R^3$ independently represents an alkyl group or a fluorinated alkyl group.

The alkyl group may be linear, branched or cyclic.

When the alkyl group is linear or branched, it preferably has 1 to 5 carbon atoms, more preferably an ethyl group or a methyl group, and an ethyl group is particularly desirable.

When the alkyl group is cyclic, it preferably has 4 to 15 carbon atoms, more preferably 4 to 12 carbon atoms, and most preferably 5 to 10 carbon atoms. Examples of cyclic alkyl groups include groups in which one or more hydrogen atoms have been removed from a monocycloalkane or a polycycloalkane such as a bicycloalkane, tricycloalkane or tetracycloalkane. Specific examples thereof include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane. Of these, a group in which one or more hydrogen atoms have been removed from adamantane is preferable.

A fluorinated alkyl group is a group in which a part or all of the hydrogen atoms within an alkyl group excluding a methyl group has been substituted with fluorine atoms, with the provision that no fluorine atom is bonded to a carbon atom adjacent to the tertiary carbon atom to which $R^1$ to $R^3$ are bonded. The alkyl group prior to being substituted with fluorine atoms may be linear, branched or cyclic.

When the alkyl group prior to being substituted with fluorine atoms is linear or branched, it preferably has 2 to 7 carbon atoms, more preferably 2 to 5, and an n-butyl group is particularly desirable. When the alkyl group prior to being substituted with fluorine atoms is cyclic, the same cyclic alkyl groups as those described above for the "alkyl group" can be used. In the fluorinated alkyl group, it is preferable that the carbon atom to which a fluorine atom is bonded be positioned remote from the tertiary carbon atom to which $R^1$ to $R^3$ are bonded.

A preferable example of such fluorinated alkyl group includes a 4,4,4-trifluoro-n-butyl group.

In the compound (I), at least one of $R^1$ to $R^3$ is a fluorinated alkyl group. In the present invention, it is preferable that one of $R^1$ to $R^3$ be the aforementioned fluorinated alkyl group, and each of the remaining two be an alkyl group.

In general formula (I) above, the terminals of $R^2$ and $R^3$ may be mutually bonded to form a ring structure. When the terminals of $R^2$ and $R^3$ are mutually bonded to form a ring structure, it is preferable that $R^2$ and $R^3$ not be fluorinated, and $R^1$ be the aforementioned fluorinated alkyl group. As the cyclic group formed by $R^2$ and $R^3$, the same cyclic alkyl groups as those described above for the "alkyl group" can be used.

As a most preferable example of the compound (I), a compound represented by general formula (I-1) shown below can be given.

[Chemical Formula 3.]

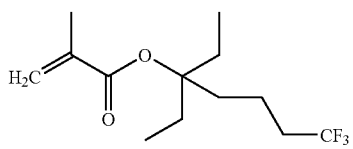

(I-1)

The production method of the compound (I) of the present invention is not particularly limited. For example, a method in which a compound (I-0-1) represented by general formula (I-0-1) shown below is reacted with a compound (I-0-2) represented by general formula (I-0-2) shown below can be preferably used.

[Chemical Formula 4.]

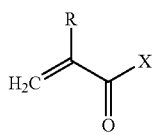

(I-0-1)

-continued

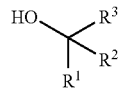

(I-0-2)

In general formula (I-0-1), R is as defined for R in general formula (I) above; and X represents a halogen atom; and in general formula (I-0-2), $R^1$ to $R^3$ are respectively as defined for $R^1$ to $R^3$ in general formula (I) above.

In general formula (I-0-1) above, examples of the halogen atom for X include a bromine atom, a chlorine atom, an iodine atom and a fluorine atom. Of these, a chlorine atom is preferable in terms of reactivity.

Further, in general formula (I-0-1) above, R and $R^1$ to $R^3$ are respectively as defined for R and $R^1$ to $R^3$ in general formula (I) above.

The reaction solvent is not particularly limited, although a reaction solvent capable of dissolving the aforementioned compounds as raw materials is preferable. Specific examples of such reaction solvents include acetonitrile and acetone.

The reaction is preferably performed in the presence of a base. The base is not particularly limited, although a base exhibiting low nucleophilicity is preferable. A specific example of such a base includes triethylamine.

Further, in terms of proceeding the reaction smoothly, the reaction is preferably performed in the presence of a catalyst. As the catalyst, any conventional catalyst can be used, and a preferable example includes 4-dimethylaminopyridine.

The reaction is preferably performed by mixing the compound (I-0-2), and preferably a base and a catalyst, with a solvent, and then dropwise adding the compound (I-0-1) thereto. The compound (I-0-1) may be diluted in advance by dissolving in a solvent. The temperature and time for dropwise adding the compound (I-0-1) can be appropriately selected depending on the raw materials to be used. The temperature is preferably −10 to 100° C., more preferably −5 to 90° C., and most preferably 0 to 80° C. The time is preferably 5 to 90 minutes, more preferably 10 to 60 minutes, and most preferably 20 to 40 minutes.

The reaction temperature and reaction time following the addition of the compound (I-0-1) can also be appropriately selected, although the reaction temperature is preferably the same as the temperature at which the compound (I-0-1) is added. The reaction time can be appropriately selected depending on the raw materials to be used, although the reaction time is preferably 0.5 to 15 hours, more preferably 1 to 10 hours, and most preferably 1.5 to 8 hours.

After the completion of the reaction, the compound of the present invention can be collected by a conventional method. For example, the reaction solution can be washed with water, a basic aqueous solution, a saline solution or the like if desired, and then the organic phase can be concentrated, and the objective compound can be crystallized. The concentrated organic phase or the crystallized objective compound can be purified by silica gel column chromatography or the like.

As the compound (I-0-2), a commercially available compound can be used, or a synthesized compound can be used. As the synthesis method of the compound (I-0-2), a conventional synthesis method of a tertiary alcohol can be used. For example, the Grignard reaction can be used, or alternatively, a silane compound having a fluorinated alkyl group can be reacted with a ketone.

The compound (I) of the present invention is a novel compound which was essentially unknown in the art.

The compound (I) can be preferably used for producing the polymeric compound of the present invention described below.

<<Polymeric Compound>>

The polymeric compound of the present invention has a structural unit (a1) represented by general formula (II) above as an essential structural unit. That is, the polymeric compound of the present invention is either a copolymer including the structural unit (a1) (hereafter, referred to as "polymeric compound (A1)"), or a polymer consisting of the structural unit (a1) (hereafter, referred to as "polymeric compound (A2)").

The structural unit (a1) is formed by the cleavage of the ethylenic double bond of the compound (I) of the present invention described above.

In general formula (II), R, $R^1$, $R^2$ and $R^3$ are respectively as defined for R, $R^1$, $R^2$ and $R^3$ in general formula (I) above.

In the structural unit (a1), when acid is generated upon exposure from an acid-generator component (B) which is blended with the polymeric compound of the present invention within the positive resist composition of the present invention described below, the linkage between the oxygen atom bonded to the carbonyl group within general formula (II) and the carbon atom to which $R^1$ to $R^3$ are bonded is broken by the action of the generated acid, and the terminal portion including $R^1$ to $R^3$ (—$C(R^1)(R^2)(R^3)$) is dissociated. Due to the dissociation of the terminal portion, the alkali solubility of the entire polymeric compound is increased.

As the structural unit (a1), one type of structural unit may be used alone, or two or more types may be used in combination.

[Polymeric Compound (A1)]
<Structural Unit (a1)>

The polymeric compound (A1) is a copolymer including the structural unit (a1).

In the polymeric compound (A1), the amount of the structural unit (a1) based on the combined total of all structural units constituting the polymeric compound (A1) is preferably 10 mol % or more, more preferably 10 to 80 mol %, still more preferably 20 to 60 mol %, and most preferably 25 to 50 mol %. By ensuring that the amount of the structural unit (a1) is at least as large as the lower limit of the above-mentioned range, a pattern can be formed when the polymeric compound is blended within a positive resist composition. On the other hand, by ensuring that the amount of the structural unit (a1) is no more than the upper limit of the above-mentioned range, a good balance can be achieved with the other structural units, and the lithography properties are improved.

<Structural Unit (a2)>

The polymeric compound (A1) preferably includes a structural unit (a2) derived from an acrylate ester containing a lactone-containing cyclic group, as well as the structural unit (a1).

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the polymeric compound (A1) is used for forming a resist film, the lactone-containing cyclic group of the structural unit (a2) is effective in improving the adhesion between the resist film and the substrate, and increasing the compatibility with the developing solution.

In the present descriptions and the claims, the term "structural unit derived from an acrylate ester" refers to a structural unit which is formed by the cleavage of the ethylenic double bond of an acrylate ester.

The term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. Examples of substituents include a halogen atom, a lower alkyl group and a halogenated lower alkyl group. Examples of halogen atoms include a fluorine atom, a chlorine atom, a bromine atom and an iodine atom, and a fluorine atom is particularly desirable.

With respect to the "structural unit derived from an acrylate ester", the "α-position (the carbon atom on the α-position)" refers to the carbon atom having the carbonyl group bonded thereto, unless specified otherwise.

With respect to the acrylate ester, specific examples of the lower alkyl group for the substituent at the α-position include linear or branched alkyl groups such as a methyl group, ethyl group, propyl group, isopropyl group, n-butyl group, isobutyl group, tert-butyl group, pentyl group, isopentyl group, and neopentyl group.

In the present invention, it is preferable that a hydrogen atom, a halogen atom, a lower alkyl group or a halogenated lower alkyl group is bonded to the α-position of the acrylate ester, more preferably a hydrogen atom, a fluorine atom, a lower alkyl group or a fluorinated lower alkyl group. In terms of industrial availability, a hydrogen atom or a methyl group is particularly desirable.

As the structural unit (a2), there is no particular limitation, and an arbitrary structural unit may be used.

Specific examples of lactone-containing monocyclic groups include groups in which one hydrogen atom has been removed from γ-butyrolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 5.]

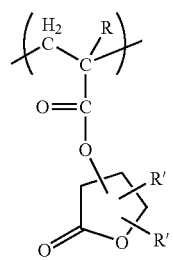
(a2-1)

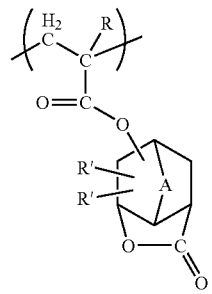
(a2-2)

-continued

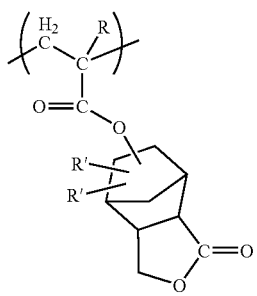
(a2-3)

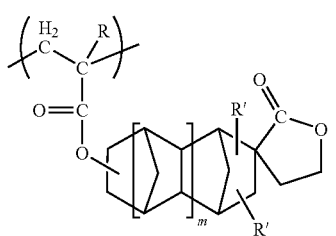
(a2-4)

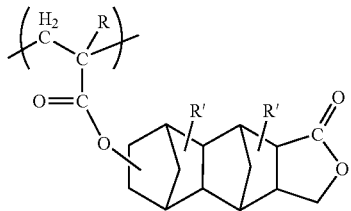
(a2-5)

In the formulas above, R represents a hydrogen atom, a halogen atom, a lower alkyl group or a halogenated lower alkyl group; R' represents a hydrogen atom, a lower alkyl group or an alkoxy group of 1 to 5 carbon atoms; m represents 0 or 1; and A represents an alkylene group of 1 to 5 carbon atoms or an oxygen atom.

In general formulas (a2-1) to (a2-5), as a halogen atom, a lower alkyl group and a halogenated lower alkyl group for R, the same halogen atoms, lower alkyl groups and halogenated lower alkyl groups as those described above which may be bonded to the α-position of the aforementioned acrylate ester can be used.

As the lower alkyl group for R', the same lower alkyl groups are those described above which may be bonded to the α-position of the aforementioned acrylate ester can be used.

Specific examples of alkylene groups of 1 to 5 carbon atoms for A include a methylene group, ethylene group, n-propylene group and isopropylene group.

In the structural units represented by general formulas (a2-1) to (a2-5), in consideration of industrial availability, R' is preferably a hydrogen atom.

Specific examples of structural units represented by general formulas (a2-1) to (a2-5) above are shown below.

[Chemical Formula 6.]

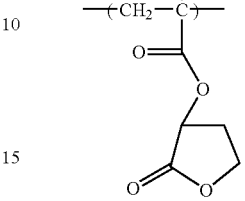
(a2-1-1)

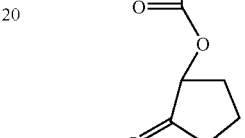
(a2-1-2)

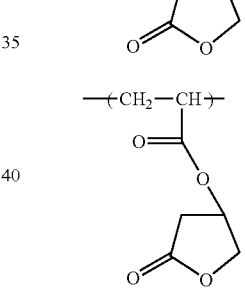
(a2-1-3)

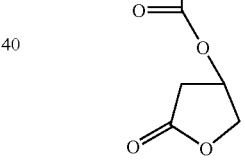
(a2-1-4)

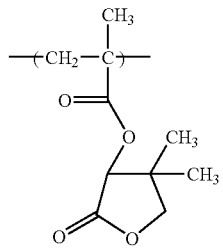
(a2-1-5)

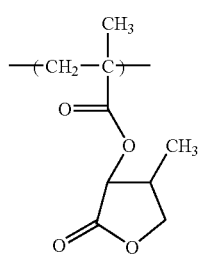
(a2-1-6)

[Chemical Formula 7.]
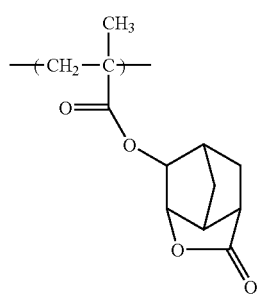 (a2-2-1)
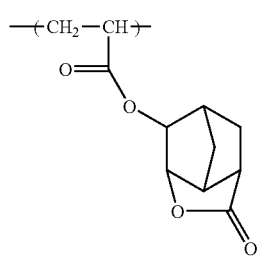 (a2-2-2)
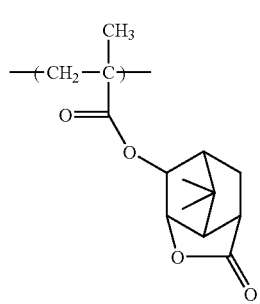 (a2-2-3)
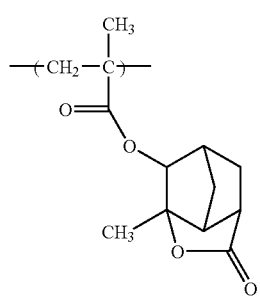 (a2-2-4)
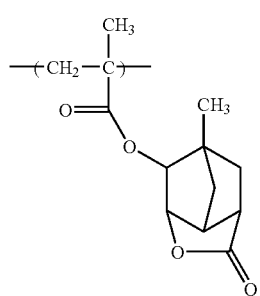 (a2-2-5)
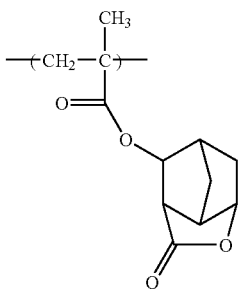 (a2-2-6)
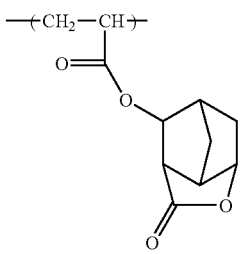 (a2-2-7)
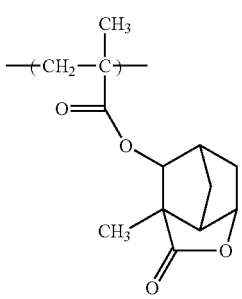 (a2-2-8)
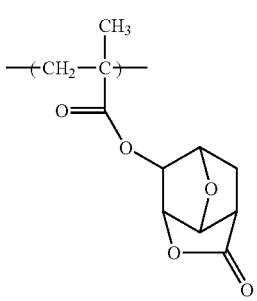 (a2-2-9)
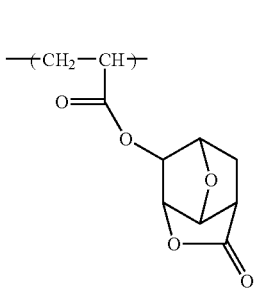 (a2-2-10)

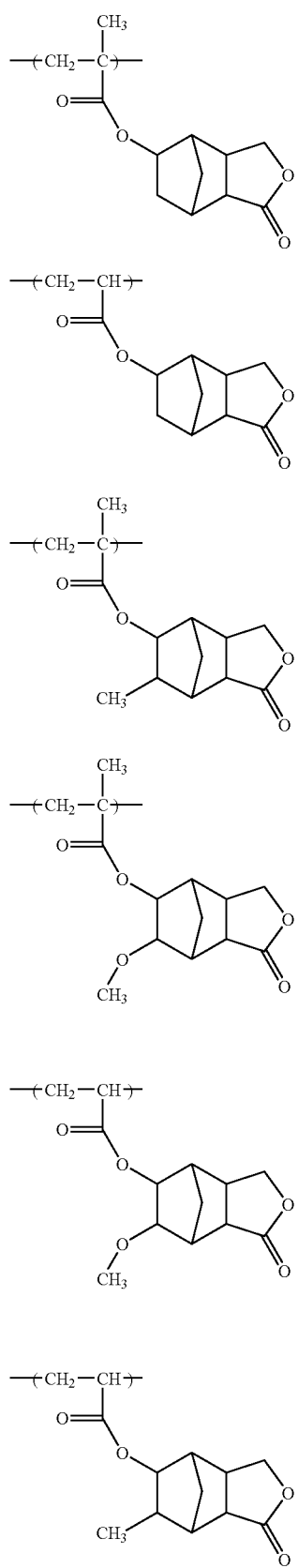
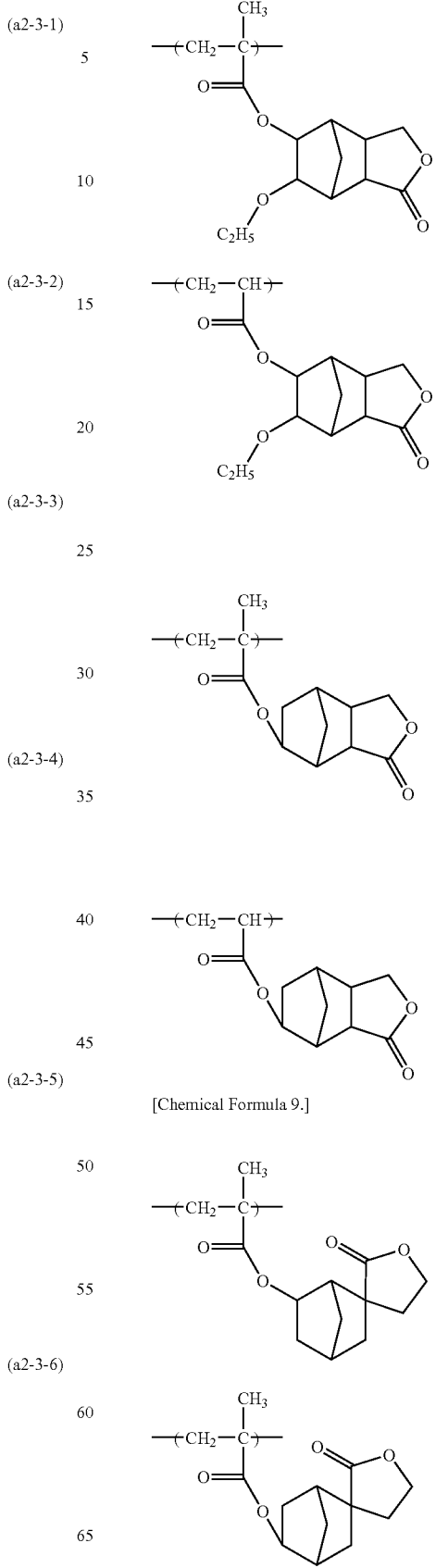

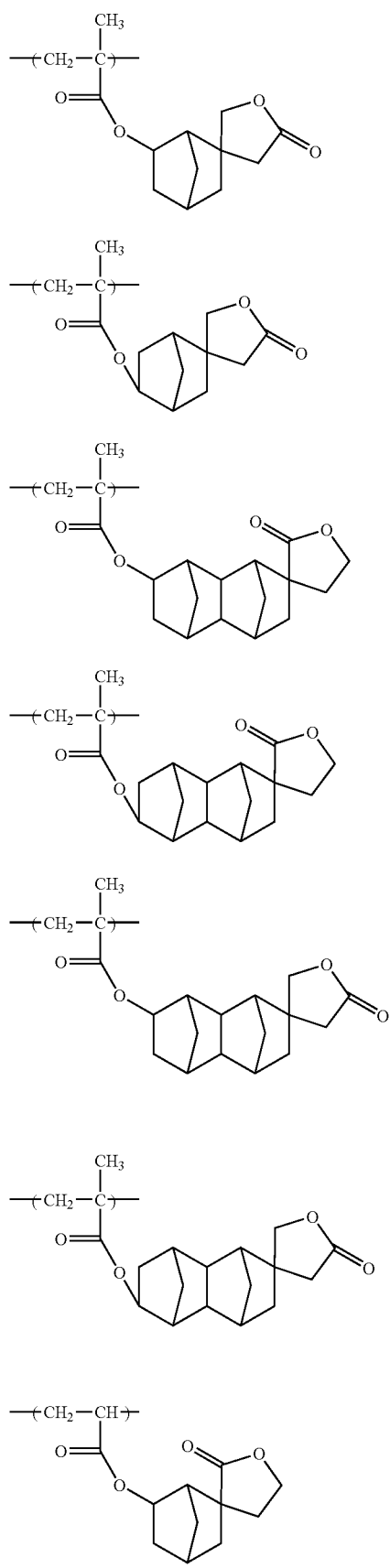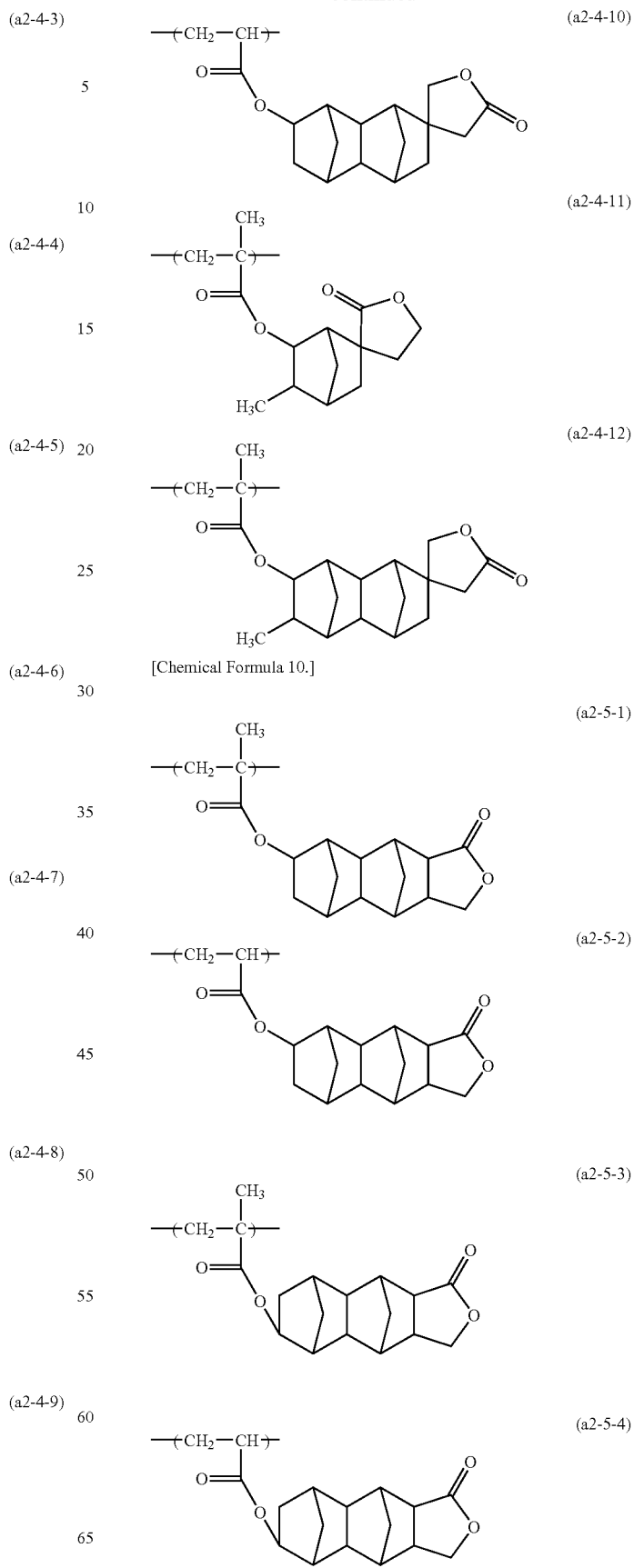
[Chemical Formula 10.]

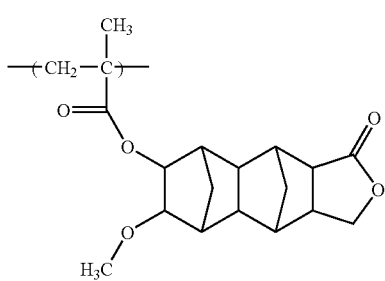

(a2-5-5)

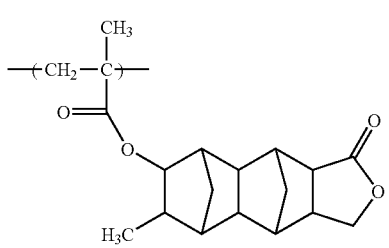

(a2-5-6)

In general formulas (a2-1) to (a2-5) above, R' is preferably a hydrogen atom in terms of industrial availability.

Among these examples, it is preferable to use at least one structural unit selected from the group consisting of a structural unit represented by general formula (a2-1), a structural unit represented by general formula (a2-2), and s structural units represented by general formula (a2-3). Specifically, it is preferable to use at least one structural unit selected from the group consisting of formulas (a2-1-1), (a2-1-2), (a2-2-1), (a2-2-2), (a2-3-1), (a2-3-2), (a2-3-9) and (a2-3-10).

In the polymeric compound (A1), as the structural unit (a2), one type of structural unit may be used, or two or more types may be used in combination.

In the polymeric (A1), the amount of the structural unit (a2) based on the combined total of all structural units constituting the polymeric compound (A1) is preferably 5 to 80 mol %, more preferably 10 to 60 mol %, and still more preferably 20 to 60 mol %. By ensuring that the amount of the structural unit (a2) is at least as large as the lower limit of the above-mentioned range, the effect of using the structural unit (a2) can be satisfactorily achieved. On the other hand, by ensuring that the amount of the structural unit (a2) is no more than the upper limit of the above-mentioned range, a good balance can be achieved with the other structural units.

<Structural Unit (a3)>

The polymeric compound preferably includes a structural unit (a3) derived from an acrylate ester containing a polar group-containing aliphatic hydrocarbon group, as well as the structural unit (a1), or the structural unit (a1) and the structural unit (a2). When the polymeric compound (A1) includes the structural unit (a3), the hydrophilicity of the polymeric compound (A1) is improved, and hence, the compatibility of the polymeric compound (A1) with the developing solution is improved. As a result, the alkali solubility of the exposed portions improves, which contributes to favorable improvements in the resolution.

Examples of the polar group include a hydroxyl group, cyano group, carboxyl group, or hydroxyalkyl group in which a part of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, cyano group, carboxyl group or a hydroxyalkyl group in which a part of the hydrogen atoms of the alkyl group have been substituted with fluorine atoms are particularly desirable. Examples of polycyclic groups include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2), and (a3-3) shown below are preferable.

[Chemical Formula 11.]

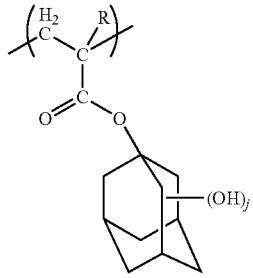

(a3-1)

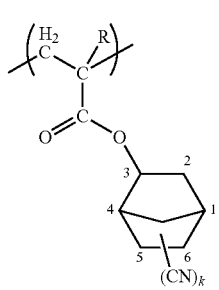

(a3-2)

(a3-3)

$$\left(\begin{array}{c}H_2 \\ C \\ \end{array}\begin{array}{c}R \\ C \\ \end{array}\right)$$

[structure with adamantyl group numbered 1-6, with (CH$_2$)$_l$ and F$_{2s+1}$C$_s$—C$_s$F$_{2s+1}$ with OH, subscript $t'$]

In the formulas above, R is as defined for R in general formula (I) above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

In formula (a3-2), k is preferably 1. The cyano group is preferably bonded to the 5th or 6th position of the norbonyl group.

In formula (a3-3), t' is preferably 1, l is preferably 1 and s is preferably 1. Further, in formula (a3-3), it is preferable that a 2-norbonyl group or 3-norbonyl group be bonded to the terminal of the carboxy group of the acrylic acid. The fluorinated alkyl alcohol is preferably bonded to the 5th or 6th position of the norbonyl group.

As the structural unit (a3), one type of structural unit may be used, or two or more types may be used in combination.

When the polymeric compound (A1) contains the structural unit (a3), the amount of structural unit (a3) based on the combined total of all structural units constituting the polymeric compound (A1) is preferably 5 to 50 mol %, more preferably 5 to 40 mol %, and still more preferably 5 to 25 mol %. By ensuring that the amount of the structural unit (a3) is at least as large as the lower limit of the above-mentioned range, the effect of using the structural unit (a3) can be satisfactorily achieved. On the other hand, by ensuring that the amount of the structural unit (a3) is no more than the upper limit of the above-mentioned range, a good balance can be achieved with the other structural units.

<Other Structural Units>

The polymeric compound (A1) may also have a structural unit other than the above-mentioned structural units (a1) to (a3), as long as the effects of the present invention are not impaired. As such a structural unit, any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used. Specific examples of other structural units include structural units (a1') and (a4) described below.

[Structural Unit (a1')]

The structural unit (a1') is a structural unit derived from an acrylate ester containing an acid dissociable, dissolution inhibiting group, and which does not fall within the category of the aforementioned structural unit (a1).

As the acid-dissociable, dissolution-inhibiting group in the structural unit (a1'), any of the groups that have been proposed as acid dissociable, dissolution inhibiting groups for the base resins of chemically amplified resists can be used.

Generally, groups that form either a cyclic or chain-like tertiary alkyl ester with the carboxyl group of the (meth) acrylic acid, and acetal-type acid dissociable, dissolution inhibiting groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

The term "aliphatic branched" refers to a branched structure having no aromaticity.

The "aliphatic branched, acid dissociable, dissolution inhibiting group" is not limited to be constituted of only carbon atoms and hydrogen atoms (not limited to hydrocarbon groups), but is preferably a hydrocarbon group.

Further, the "hydrocarbon group" may be either saturated or unsaturated, but is preferably saturated.

Examples of aliphatic branched, acid dissociable, dissolution inhibiting groups include tertiary alkyl groups of 4 to 8 carbon atoms, and specific examples include a tert-butyl group, tert-amyl group and tert-heptyl group.

In the "aliphatic cyclic group-containing acid dissociable, dissolution inhibiting group", as the aliphatic cyclic group, an aliphatic cyclic group of 4 to 12 carbon atoms can be preferably used.

In the present description and claims, the term "aliphatic" is a relative concept used in relation to the term "aromatic", and defines a group or compound that has no aromaticity. The "aliphatic cyclic group" within the structural unit (a1) may or may not have a substituent.

The aliphatic cyclic group may or may not have a substituent. Examples of substituents include a lower alkyl group of 1 to 5 carbon atoms and an oxygen atom (=O). The aliphatic cyclic group "has a substituent" means that a substituent is directly bonded to an atom that constitutes the ring of the aliphatic cyclic group.

The basic ring of the "aliphatic cyclic group" exclusive of substituents is not limited to be a ring consisting of carbon and hydrogen (not limited to hydrocarbon rings), but is preferably a hydrocarbon ring.

The "hydrocarbon group" may be either saturated or unsaturated, but is preferably saturated.

The "aliphatic cyclic group" may be either a monocyclic group or a polycyclic group. In terms of etching resistance and the like, the aliphatic cyclic group is preferably a polycyclic group.

Specific examples of monocyclic groups for the aliphatic cyclic group include groups in which one or more hydrogen atoms have been removed from a monocycloalkane. Examples of monocycloalkanes include cyclopentane and cyclohexane.

Specific examples of polycyclic groups for the aliphatic cyclic group include groups in which one or more hydrogen atoms have been removed from a polycycloalkane (e.g., a bicycloalkane, a tricycloalkane, a tetracycloalkane, or the like). Examples of polycycloalkanes include adamantane, norbornane, isobornane, tricyclodecane and tetracyclododecane.

The aliphatic cyclic group preferably has 1 to 3 substituents, more preferably 1 or 2 substituents, and most preferably 1 substituent. The bonding position of the substituent is not particularly limited.

As the aliphatic cyclic group-containing acid dissociable, dissolution inhibiting group, for example, a group which has a tertiary carbon atom on the ring structure of the cycloalkyl group can be used. Specific examples include 2-methyl-2-adamantyl group and a 2-ethyl-2-adamantyl group. Further, groups having an aliphatic cyclic group such as an adamantyl group, and a branched alkylene group having a tertiary carbon atom bonded thereto, as the groups bonded to the oxygen atom of the carbonyl group (—C(O)—O—) within the structural units represented by general formula (a1″) shown below, can be used.

[Chemical Formula 12.]

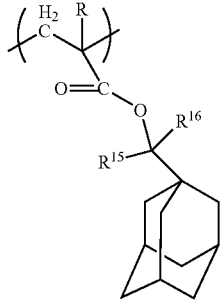

(a1″)

In the formula above, R is as defined for R in general formula (I) above; and each of $R^{15}$ and $R^{16}$ independently represents an alkyl group (which may be linear or branched, and preferably has 1 to 5 carbon atoms).

An "acetal-type acid dissociable, dissolution inhibiting group" generally substitutes a hydrogen atom at the terminal of an alkali-soluble group such as a carboxy group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 13.]

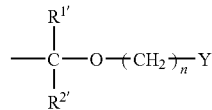

(p1)

In the formula above, $R^{1\prime}$ and $R^{2\prime}$ each independently represents a hydrogen atom or a lower alkyl group; n represents an integer of 0 to 3; and Y represents a lower alkyl group or an aliphatic cyclic group.

In general formula (p1) above, n is preferably an integer of 0 to 2, more preferably 0 or 1, and most preferably 0.

As the lower alkyl group for $R^{1\prime}$ and $R^{2\prime}$, the same as the lower alkyl groups for R above can be used. As the lower alkyl group for $R^{1\prime}$ and $R^{2\prime}$, a methyl group or ethyl group is preferable, and a methyl group is particularly desirable.

In the present invention, it is preferable that at least one of $R^{1\prime}$ and $R^{2\prime}$ be a hydrogen atom. That is, it is preferable that the acid dissociable, dissolution inhibiting group (p1) is a group represented by general formula (p1-1) shown below.

[Chemical Formula 14.]

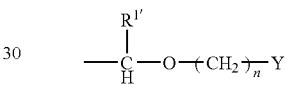

(p1-1)

In the formula above, $R^{1\prime}$, n and Y are respectively as defined for $R^{1\prime}$, n and Y in general formula (p1) above.

As the lower alkyl group for Y, the same lower alkyl groups as those described above for R in general formula (I) can be used.

As the aliphatic cyclic group for Y, any of the aliphatic monocyclic/polycyclic groups which have been proposed for conventional ArF resists and the like can be appropriately selected for use. For example, the aliphatic cyclic groups described above for the aforementioned "aliphatic cyclic group-containing acid dissociable, dissolution inhibiting group" (which may have, as a substituent, a fluorine atom or a fluorinated alkyl group of 1 to 5 carbon atoms) can be used.

Further, as the acetal-type, acid dissociable, dissolution inhibiting group, groups represented by general formula (p2) shown below can also be used.

[Chemical Formula 15.]

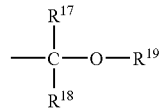

(p2)

In the formula above, $R^{17}$ and $R^{18}$ each independently represents a linear or branched alkyl group or a hydrogen atom; and $R^{19}$ represents a linear, branched or cyclic alkyl group; or $R^{17}$ and $R^{19}$ each independently represents a linear or branched alkylene group, wherein the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane. Of these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto and the carbon atom having the oxygen atom and $R^{17}$ bonded thereto. Such a cyclic group is preferably a 4 to 7-membered ring, and more preferably a 4 to 6-membered ring. Specific examples of the cyclic group include tetrahydropyranyl group and tetrahydrofuranyl group.

As the structural unit (a1'), it is preferable to use at least one member selected from the group consisting of structural units represented by formula (a1-0-1) shown below and structural units represented by formula (a1-0-2) shown below.

[Chemical Formula 16.]

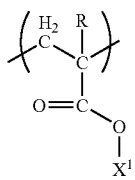

(a1-0-1)

In the formula above, R represents a hydrogen atom, a halogen atom, a lower alkyl group or a halogenated lower alkyl group; and $X^1$ represents an acid dissociable, dissolution inhibiting group.

[Chemical Formula 17.]

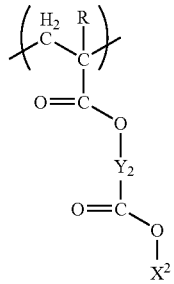

(a1-0-2)

In the formula above, R represents a hydrogen atom, a halogen atom, a lower alkyl group or a halogenated lower alkyl group; $X^2$ represents an acid dissociable, dissolution inhibiting group; and $Y^2$ represents an alkylene group or an aliphatic cyclic group.

In general formula (a1-0-1) shown above, R is as defined for R in general formula (I) above.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is as defined for R in general formula (I) above.

$X^2$ is as defined for $X^1$ in general formula (a1-0-1) above.

$Y^2$ is preferably an alkylene group of 1 to 4 carbon atoms or a divalent aliphatic cyclic group. As the aliphatic cyclic group, the same as those described above in connection with the explanation of "aliphatic cyclic group" can be used, except that two hydrogen atoms have been removed therefrom.

Specific examples of the structural unit (a1') include structural units represented by general formulas (a1-1) to (a1-4) shown below. Among these, a structural unit represented by general formula (a1-1) shown below is preferable.

[Chemical Formula 18.]

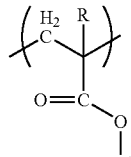

(a1-1)

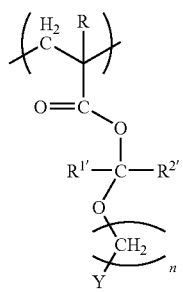

(a1-2)

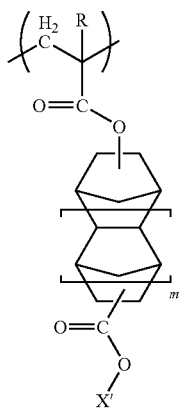

(a1-3)

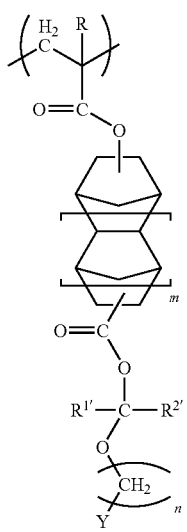

(a1-4)

In the formulas above, X' represents a tertiary alkyl ester-type acid dissociable, dissolution inhibiting group; Y represents a lower alkyl group of 1 to 5 carbon atoms or an aliphatic cyclic group; n represents an integer of 0 to 3; m represents 0 or 1; R is as defined for R in general formula (I) above; and each of $R^{1\prime}$ and $R^{2\prime}$ independently represents a hydrogen atom or a lower alkyl group of 1 to 5 carbon atoms.

It is preferable that at least one of $R^{1\prime}$ and $R^{2\prime}$ represents a hydrogen atom, and it is more preferable that both of $R^{1\prime}$ and $R^{2\prime}$ a hydrogen atom. n is preferably 0 or 1.

Examples of the tertiary alkyl ester-type acid dissociable, dissolution inhibiting group for X' include the same tertiary alkyl ester-type acid dissociable, dissolution inhibiting groups as those described above for $X^1$ in general formula (a1-0-1).

As the aliphatic cyclic group for Y, the same aliphatic cyclic groups as those described above in the explanation of "aliphatic cyclic group" can be used.

Specific examples of structural units represented by general formula (a1-1) to (a1-4) are shown below.

[Chemical Formula 19.]

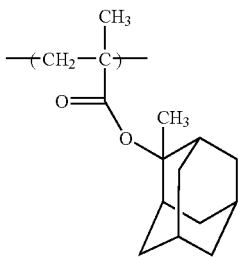

(a1-1-1)

(a1-1-2)

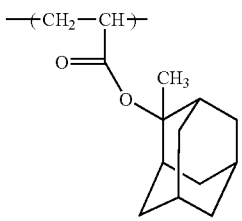

(a1-1-3)

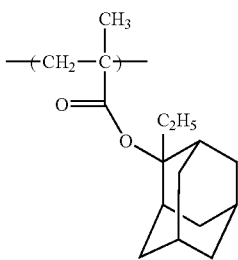

(a1-1-4)

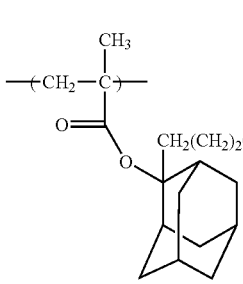

(a1-1-5)

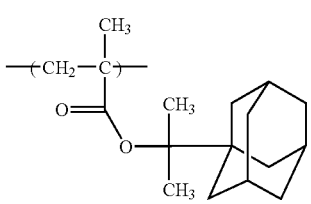

(a1-1-6)

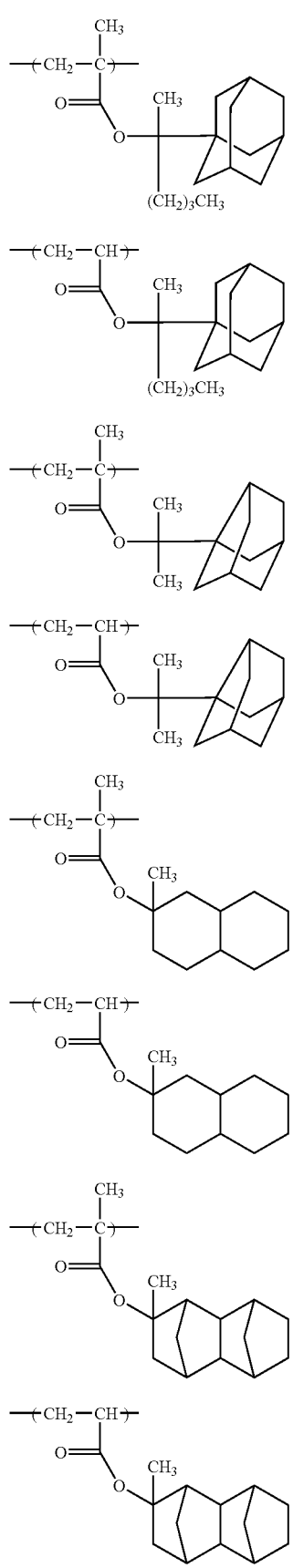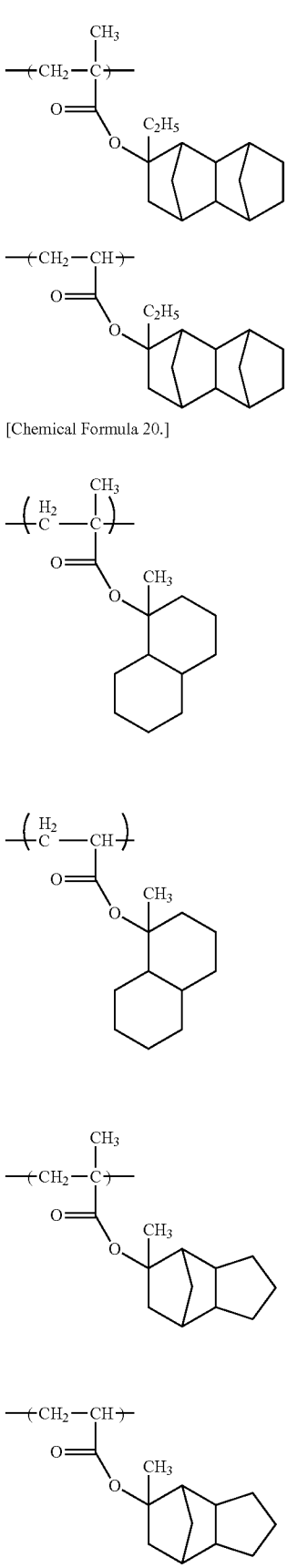

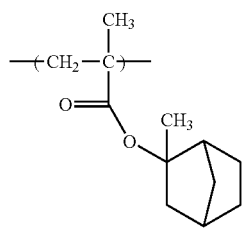
(a1-1-21)
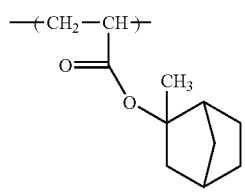
(a1-1-22)
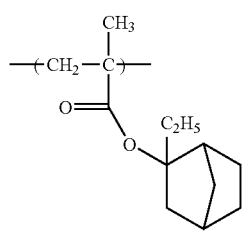
(a1-1-23)
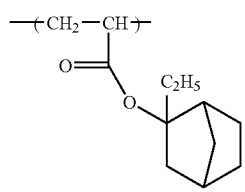
(a1-1-24)
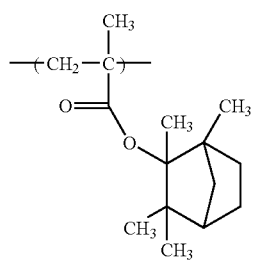
(a1-1-25)
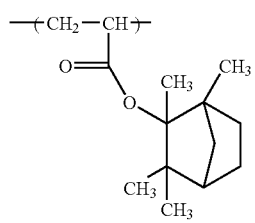
(a1-1-26)
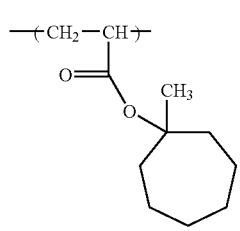
(a1-1-27)
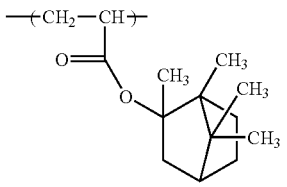
(a1-1-28)
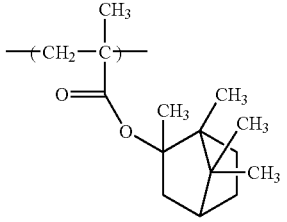
(a1-1-29)
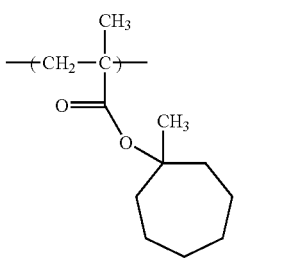
(a1-1-30)
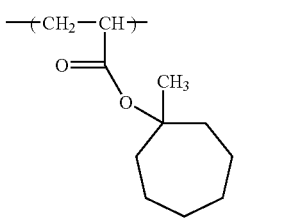
(a1-1-31)
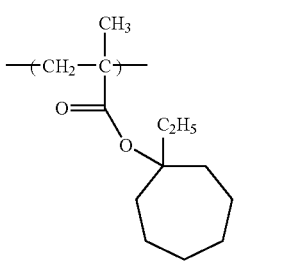
(a1-1-32)
[Chemical Formula 21.]
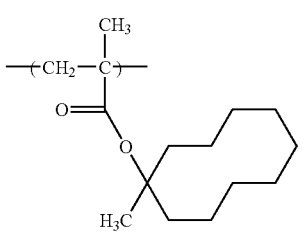
(a1-1-33)

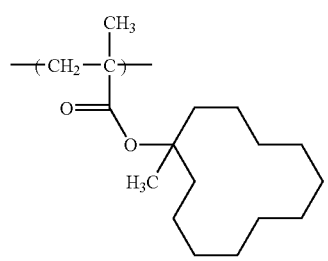
(a1-1-34)
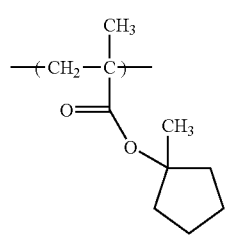
(a1-1-35)
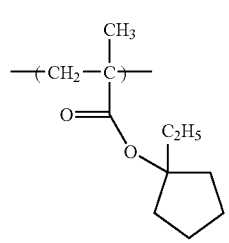
(a1-1-36)
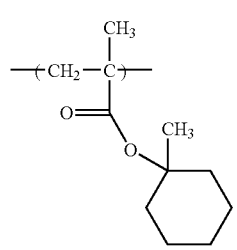
(a1-1-37)
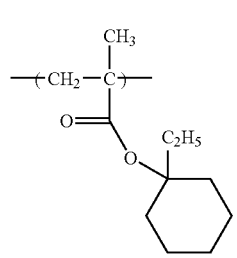
(a1-1-38)
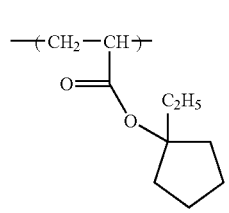
(a1-1-39)
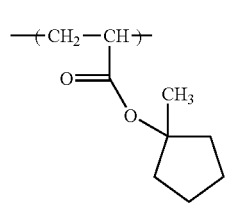
(a1-1-40)
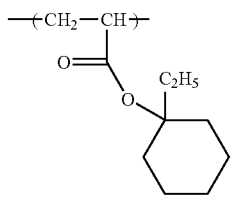
(a1-1-41)
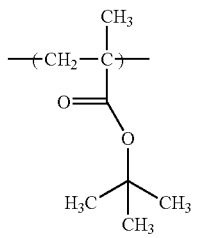
(a1-1-42)
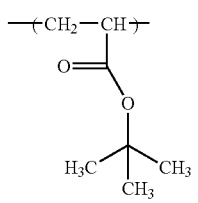
(a1-1-43)
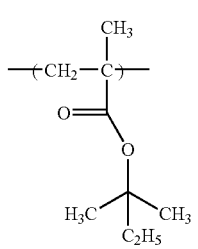
(a1-1-44)
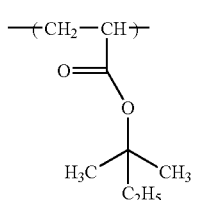
(a1-1-45)
[Chemical Formula 22.]
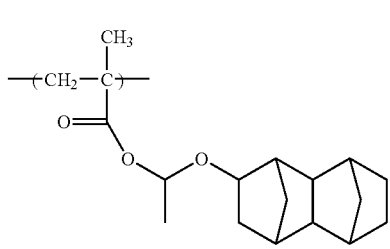
(a1-2-1)
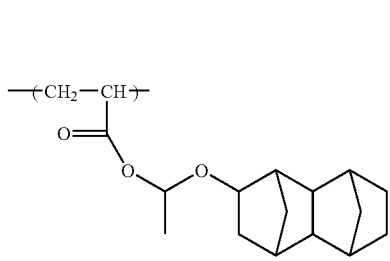
(a1-2-2)

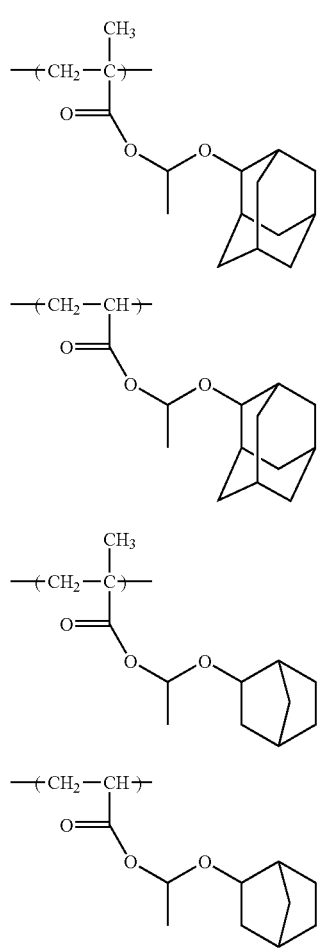
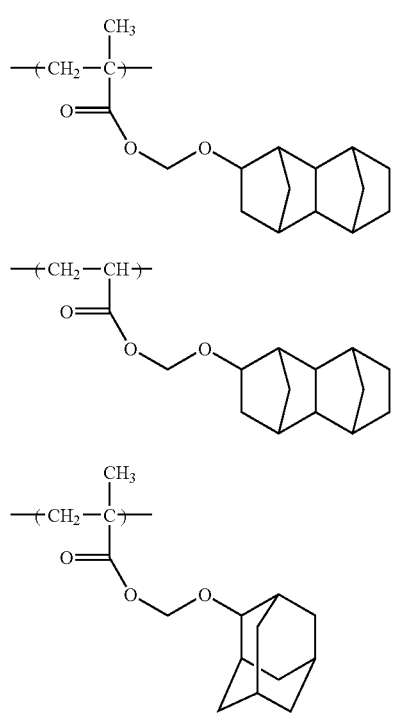
[Chemical Formula 23.]
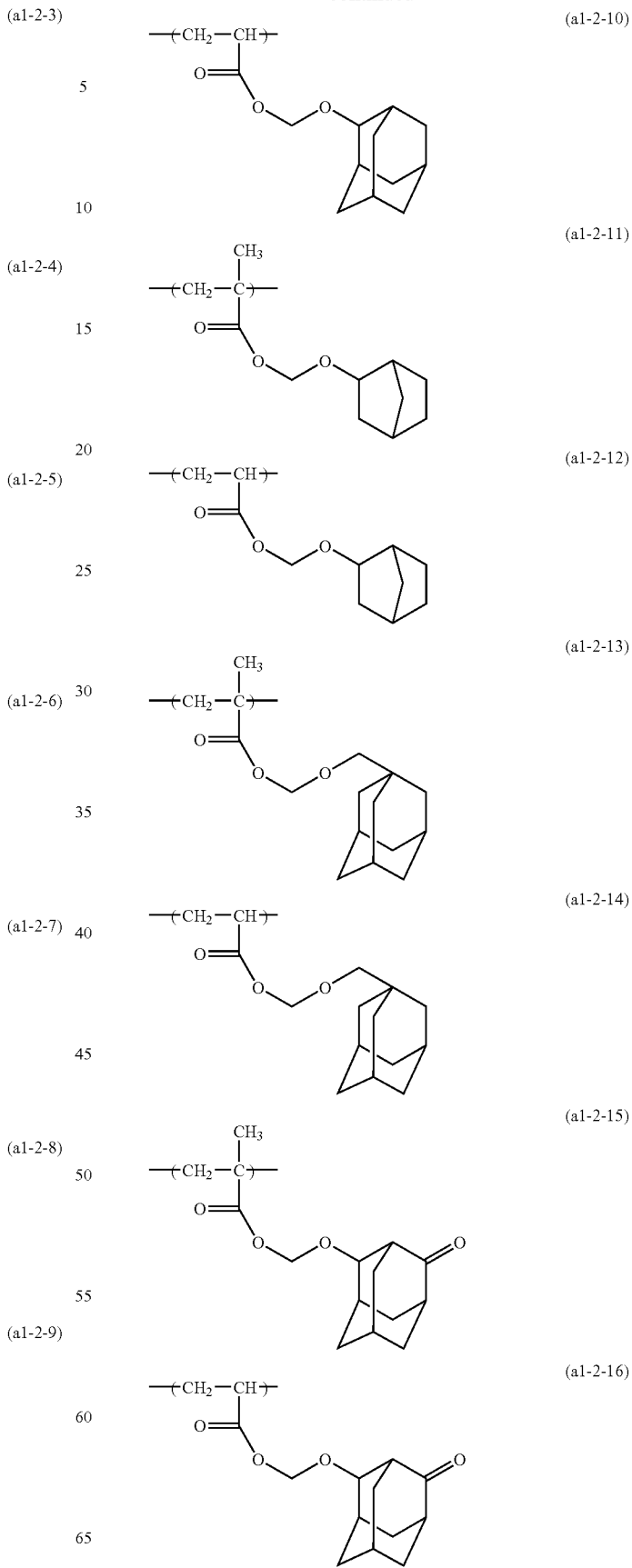

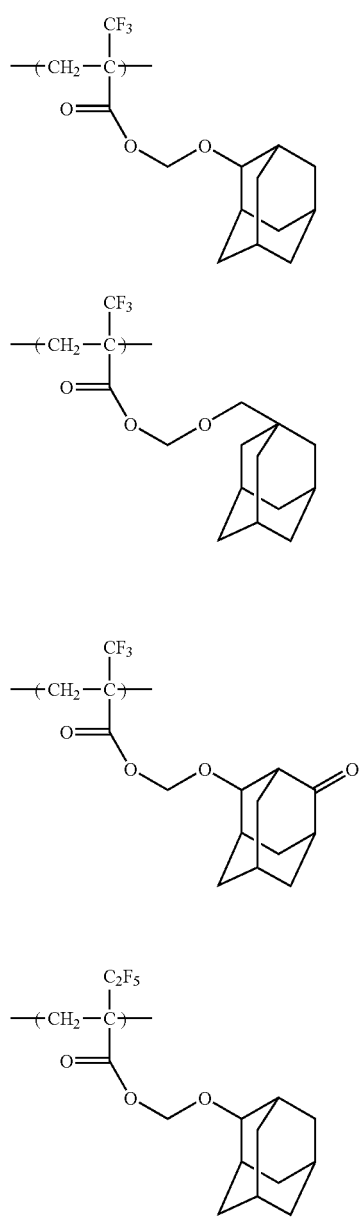
(a1-2-17)
(a1-2-18)
(a1-2-19)
(a1-2-20)
[Chemical Formula 24.]
(a1-2-21)
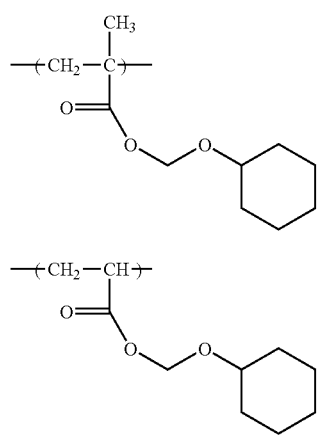
(a1-2-22)
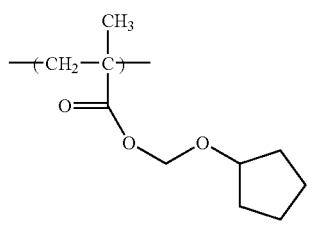
(a1-2-23)
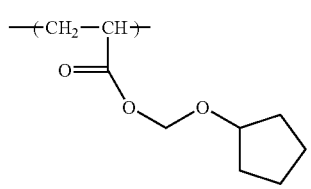
(a1-2-24)
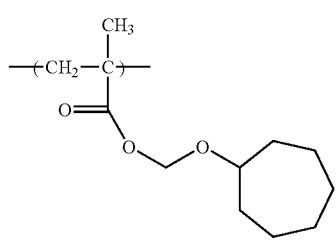
(a1-2-25)
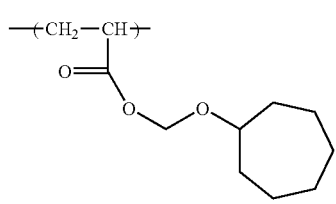
(a1-2-26)
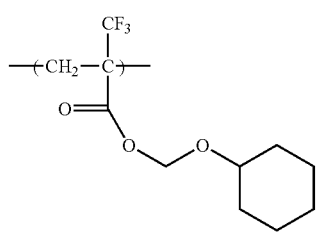
(a1-2-27)
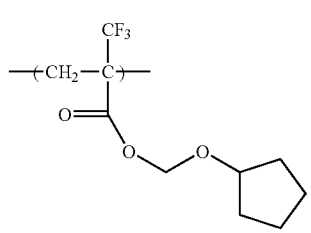
(a1-2-28)
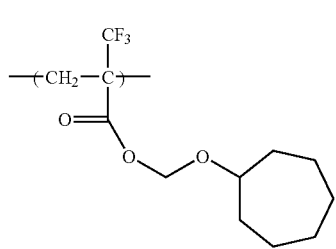
(a1-2-29)

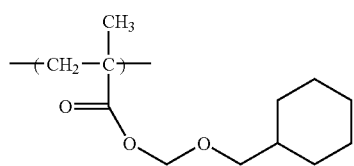
(a1-2-30)
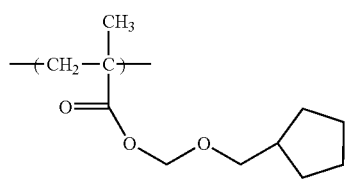
(a1-2-31)
[Chemical Formula 25.]
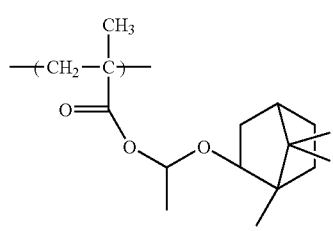
(a1-2-32)
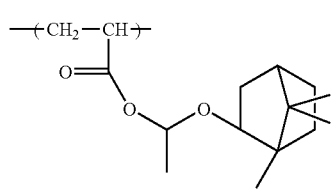
(a1-2-33)
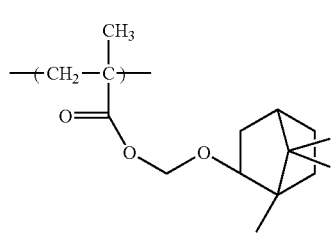
(a1-2-34)
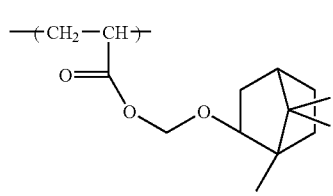
(a1-2-35)
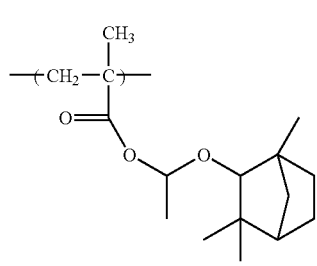
(a1-2-36)
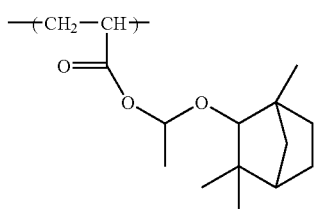
(a1-2-37)
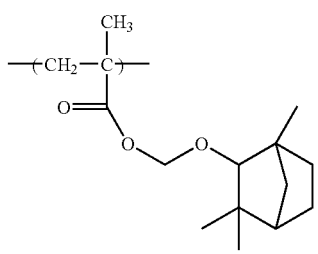
(a1-2-38)
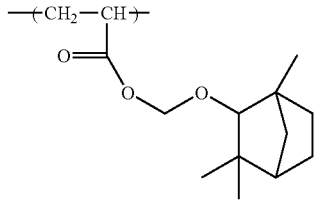
(a1-2-39)
[Chemical Formula 26.]
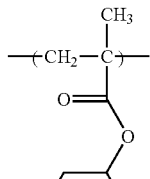
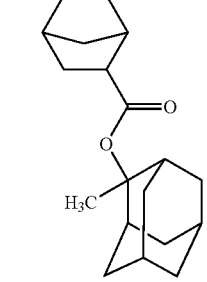
(a1-3-1)

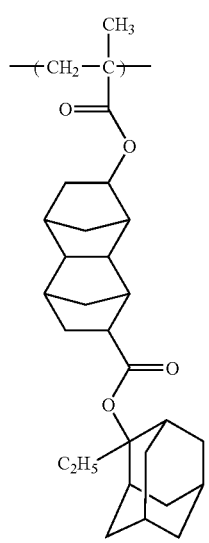 (a1-3-2)
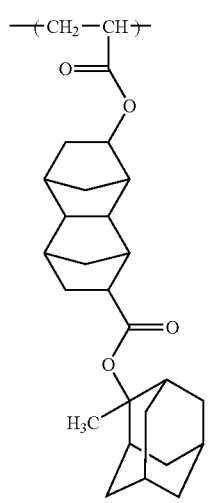 (a1-3-3)
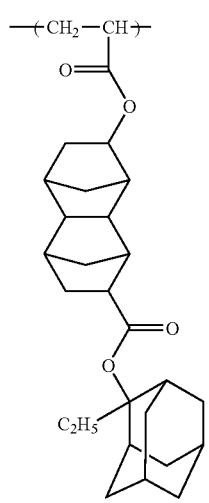 (a1-3-4)
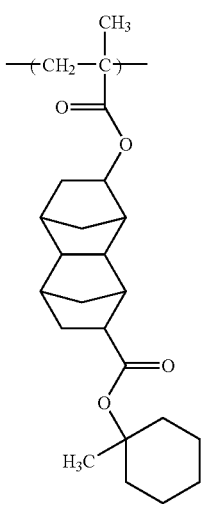 (a1-3-5)
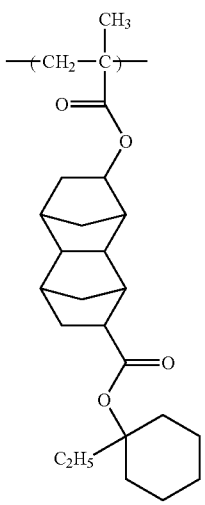 (a1-3-6)
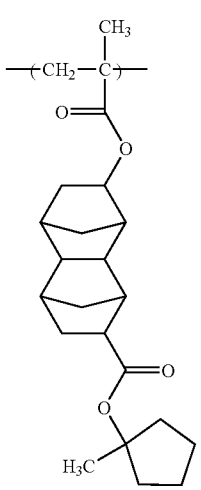 (a1-3-7)

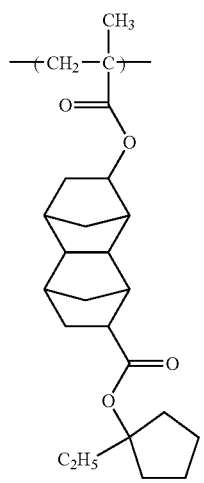 (a1-3-8)
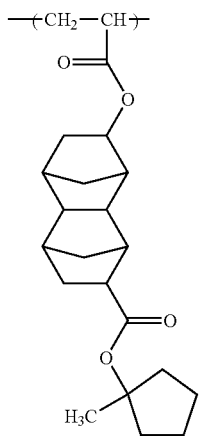 (a1-3-11)
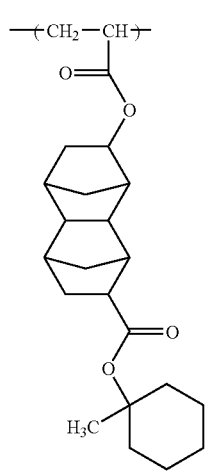 (a1-3-9)
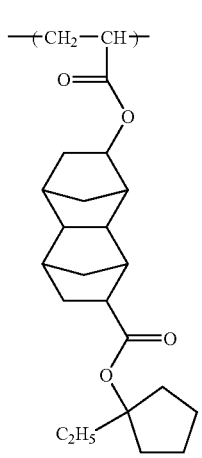 (a1-3-12)
[Chemical Formula 27.]
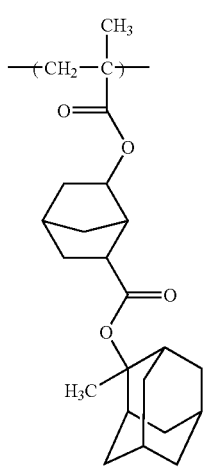 (a1-3-13)
(a1-3-10)

(a1-3-14) 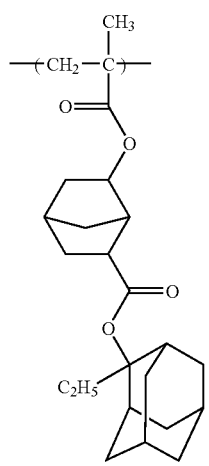
(a1-3-15) 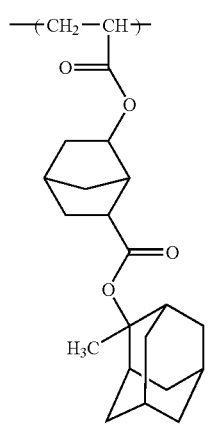
(a1-3-16) 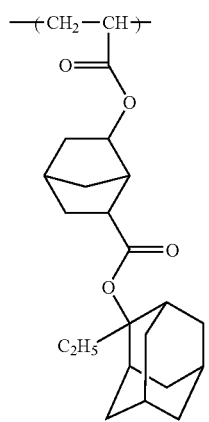
(a1-3-17) 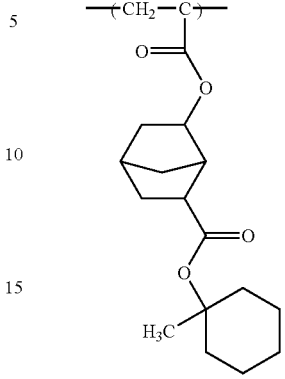
(a1-3-18) 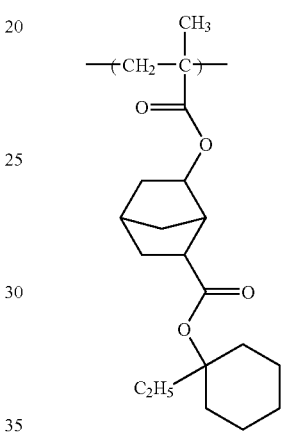
(a1-3-19) 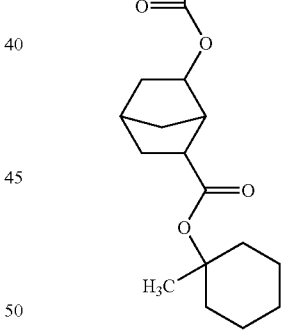
(a1-3-20) 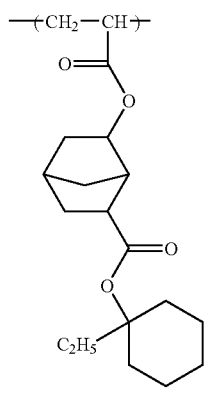

(a1-3-21)
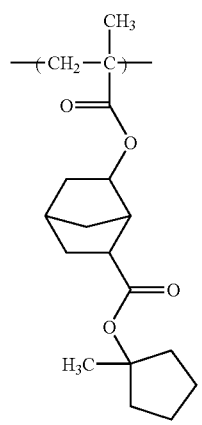
(a1-3-22)
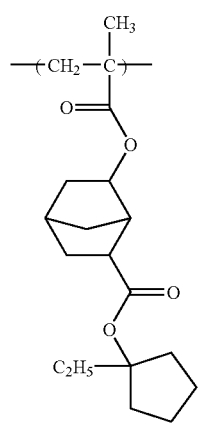
(a1-3-23)
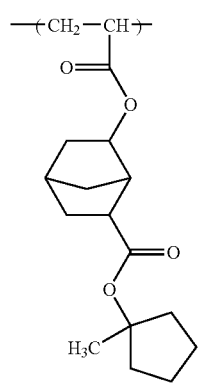
(a1-3-24)
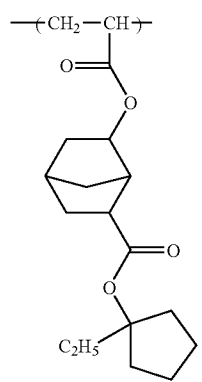
[Chemical Formula 28.]
(a1-4-1)
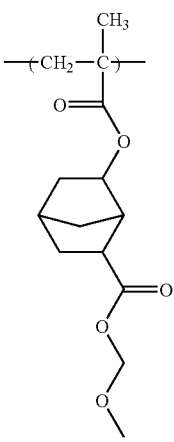
(a1-4-2)
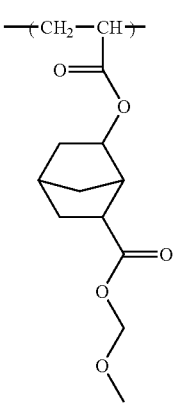
(a1-4-3)
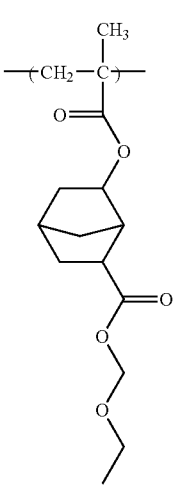

(a1-4-4)
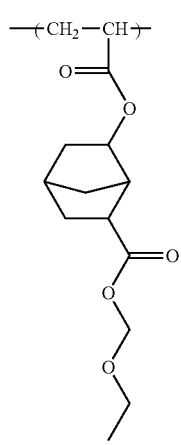
(a1-4-7)
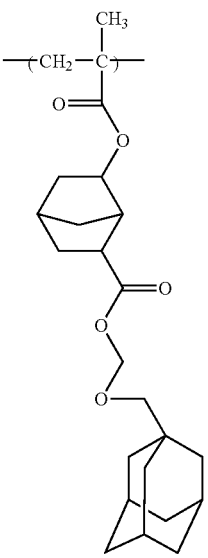
(a1-4-5)
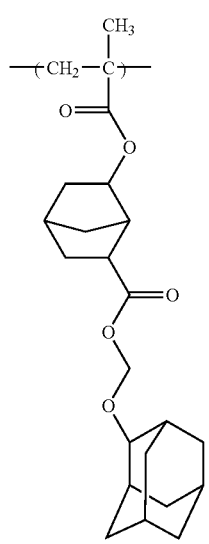
(a1-4-8)
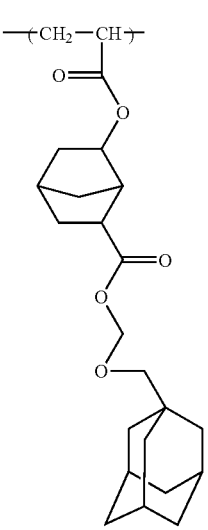
(a1-4-6)
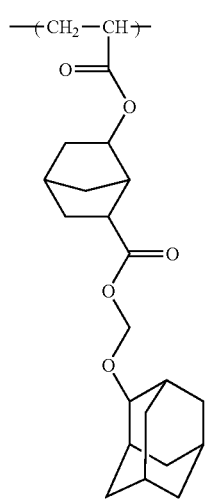
(a1-4-9)
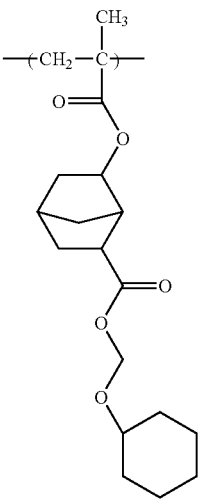

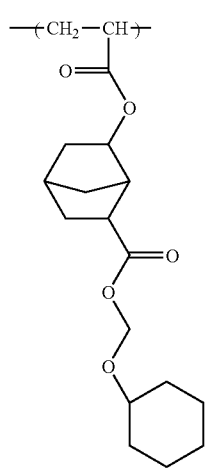
(a1-4-10)
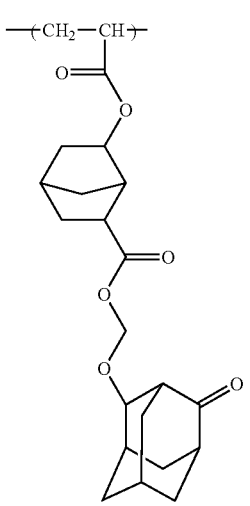
(a1-4-13)
(a1-4-11)
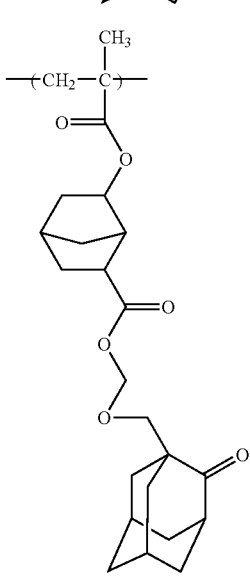
(a1-4-14)
(a1-4-12)
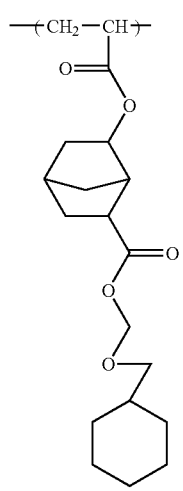
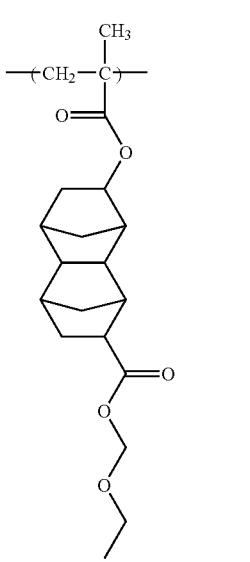
(a1-4-15)

-continued
[Chemical Formula 29.]
(a1-4-16)
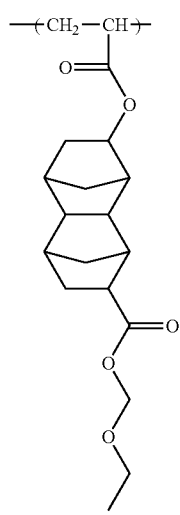
(a1-4-17)
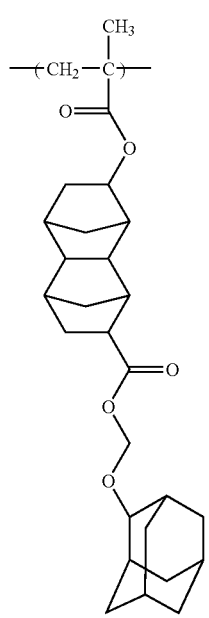
(a1-4-18)
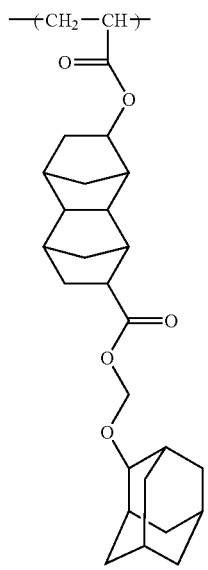
(a1-4-19)
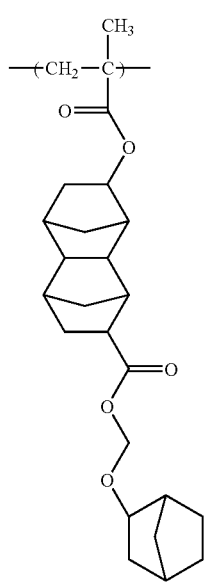
(a1-4-20)
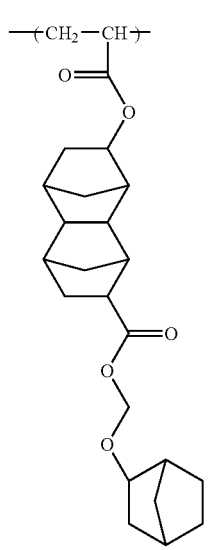

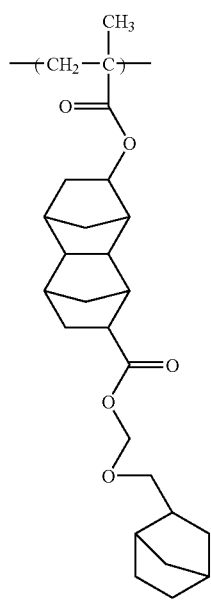
(a1-4-21)
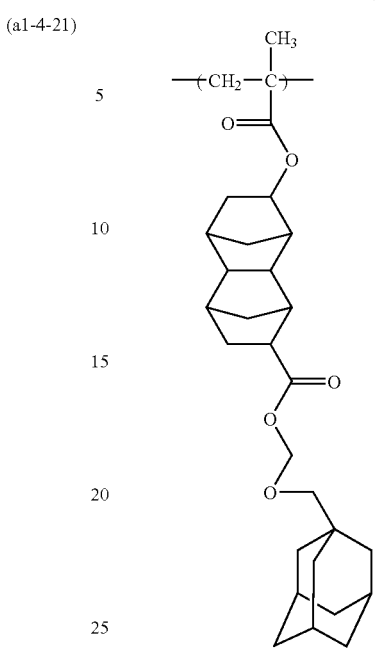
(a1-4-23)
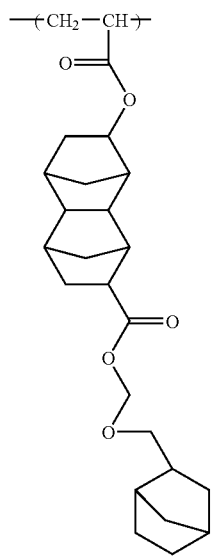
(a1-4-22)
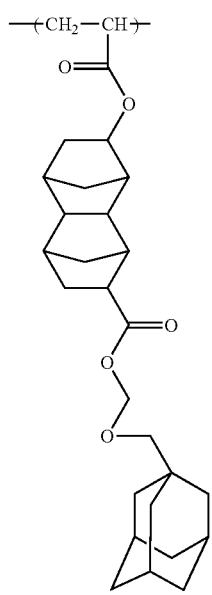
(a1-4-24)

(a1-4-25)
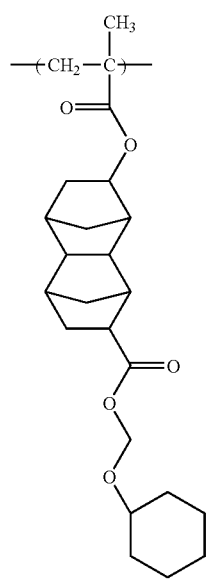
(a1-4-26)
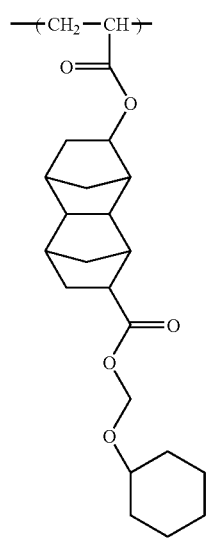
(a1-4-27)
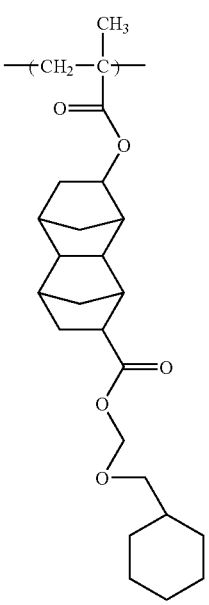
(a1-4-28)
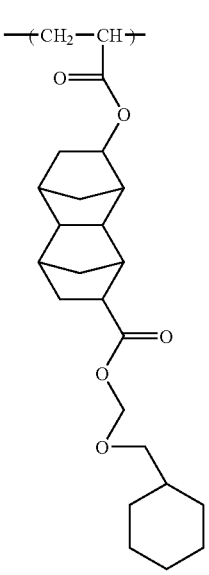

-continued

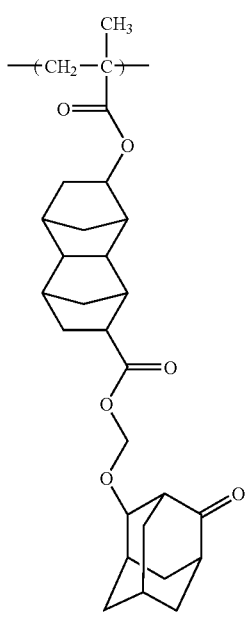
(a1-4-29)

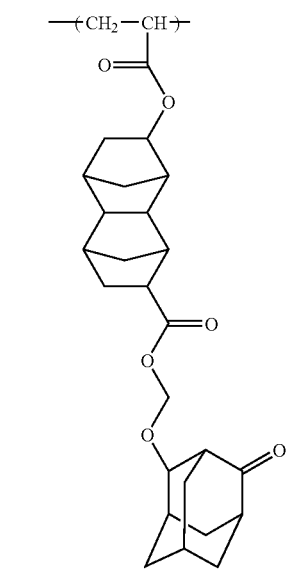
(a1-4-30)

Among these, as the structural unit (a1'), a structural unit represented by general formula (a1-1-01) shown below which includes the structural units represented by formulas (a1-1-1) to (a1-1-4), and a structural unit represented by general formula (a1-1-02) shown below which includes the structural units represented by formulas (a1-1-35) to (a1-1-41) are preferable, and a structural unit represented by general formula (a1-1-01) is particularly desirable.

[Chemical Formula 30.]

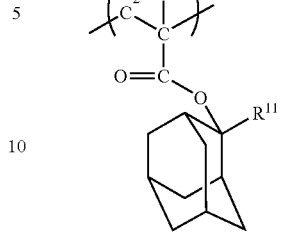
(a1-1-01)

In the formula above, R represents a hydrogen atom, a halogen atom, a lower alkyl group or a halogenated lower alkyl group; and $R^{11}$ represents a lower alkyl group.

[Chemical Formula 31.]

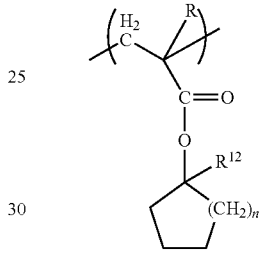
(a1-1-02)

In the formula above, R represents a hydrogen atom, a halogen atom, a lower alkyl group or a halogenated lower alkyl group; $R^{12}$ represents a lower alkyl group; and h represents an integer of 1 to 3.

In general formula (a1-1-01), R is as defined for R in general formula (I) above. The lower alkyl group for $R^{11}$ is the same as defined for the lower alkyl group for R above, and is preferably a methyl group or an ethyl group.

In general formula (a1-1-02), R is as defined for R in general formula (I) above. The lower alkyl group for $R^{12}$ is the same as defined above for the lower alkyl group for R above. $R^{12}$ is preferably a methyl group or an ethyl group, and most preferably an ethyl group. h is preferably 1 or 2, and most preferably 2.

In the polymeric compound (A1), as the structural unit (a1'), one type of structural unit may be used alone, or two or more types may be used in combination.

When the polymeric compound (A1) contains the structural unit (a1'), the amount of the structural unit (a1') based on the combined total of all structural units constituting the polymeric compound (A1) is preferably 1 to 50 mol %, more preferably 5 to 50 mol %, and still more preferably 10 to 40 mol %. By ensuring that the amount of the structural unit (a1') is at least as large as the lower limit of the above-mentioned range, a pattern can be easily formed using a positive resist composition prepared from the polymeric compound (A1). On the other hand, by ensuring that the amount of the structural unit (a1') is no more than the upper limit of the above-mentioned range, a good balance can be achieved with the other structural units.

[Structural Unit (a4)]

The structural unit (a4) is a structural unit derived from an acrylate ester containing a non-acid-dissociable aliphatic polycyclic group.

Examples of polycyclic groups include the same groups as those described above for the aforementioned aliphatic cyclic group within the structural unit (a1') which are polycyclic, and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 32.]

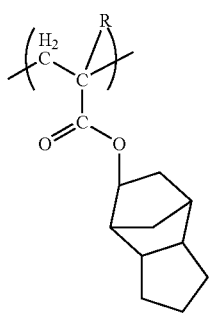
(a4-1)

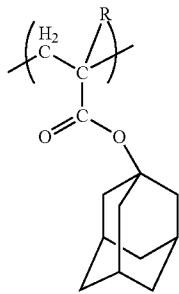
(a4-2)

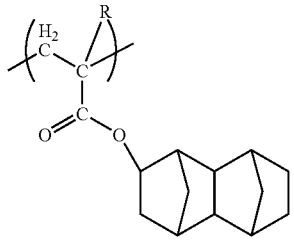
(a4-3)

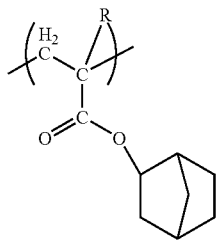
(a4-4)

-continued

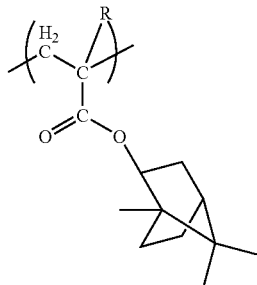
(a4-5)

In the formulas above, R is ad defined for R in general formula (I) above.

When the structural unit (a4) is included in the polymeric compound (A1), the amount of the structural unit (a4) based on the combined total of all the structural units that constitute the polymeric compound (A1) is preferably within the range from 1 to 30 mol %, and more preferably from 10 to 20 mol %.

In the present invention, the polymeric compound (A1) is preferably a copolymer including at least the structural unit (a1) and the structural unit (a2). Examples of such copolymers include a binary copolymer consisting of the structural units (a1) and (a2), a ternary copolymer consisting of the structural units (a1), (a2) and (a3), and a quaternary copolymer consisting of the structural units (a1), (a2), (a3) and (a4).

In the present invention, as the polymeric compound (A1), a copolymer consisting of the combination of three structural units as represented by general formula (A-1-1) shown below is particularly desirable (wherein R is as defined for R in general formula (I) above).

[Chemical Formula 33.]

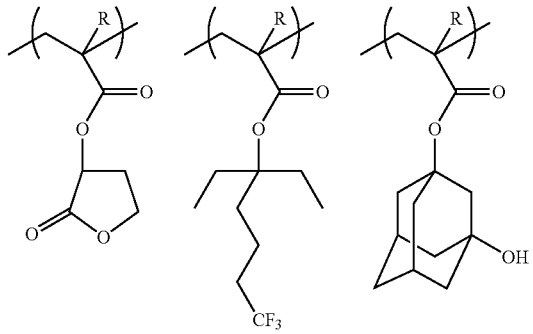
(A-1-1)

In the formula above, R is as defined for R in general formula (I) above.

The polymeric compound (A1) can be produced, for example, by a conventional radical polymerization or the like of the monomers corresponding with each of the structural units, using a radical polymerization initiator such as 2,2'-azobisisobutyronitrile (AIBN) or 2,2'-azobis(2,4-dimethylvaleronitrile).

The weight average molecular weight (Mw) (the polystyrene equivalent value determined by gel permeation chromatography) of the polymeric compound (A1) is not particularly limited, but is preferably 2,000 to 50,000, more preferably 3,000 to 30,000, and most preferably 5,000 to 20,000. By ensuring that the weight average molecular weight is no more than the upper limit of the above-mentioned range, the polymeric compound (A1) exhibits satisfactory solubility in a resist solvent when used as a resist. On the other hand, by ensuring that the weight average molecular weight is at least as large as the lower limit of the above-mentioned range, dry etching resistance and cross-sectional shape of the resist pattern becomes satisfactory.

Further, the dispersity (Mw/Mn) is preferably 1.0 to 5.0, and more preferably 1.0 to 3.0. Here, Mn is the number average molecular weight.

The polymeric compound (A1) of the present invention is a novel compound which was essentially unknown in the art.

The polymeric compound (A1) is useful as a base resin for a chemically amplified positive resist composition, and can be preferably used as the component (A) of the positive resist composition described below.

[Polymeric Compound (A2)]

The polymeric compound (A2) is a polymer consisting of the aforementioned structural unit (a1).

The polymeric compound (A2) of the present invention is a novel compound which was also essentially unknown in the art. The polymeric compound (A2) can be used in combination with a base resin for a conventional chemically amplified positive resist composition to exhibit the same effects as the polymeric compound (A1). Therefore, the polymeric compound (A2) can be preferably used as the component (A) of the positive resist composition described below.

In the present invention, as the polymeric compound (A2), a polymer represented by general formula (A-2-1) shown below can be given as a most preferable example (wherein R is as defined for R in general formula (I) above).

[Chemical Formula 34.]

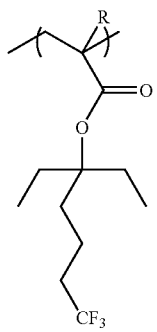

(A'-2-1)

In the formula above, R is as defined for R in general formula (I) above.

The polymeric compound (A2) can be produced, for example, by a conventional radical polymerization or the like of a compound represented by general formula (I) above as the monomer, using a radical polymerization initiator such as 2,2'-azobisisobutyronitrile (AIBN) or 2,2'-azobis(2,4-dimethylvaleronitrile).

The preferable weight average molecular weight (Mw) (the polystyrene equivalent value determined by gel permeation chromatography) and dispersity (Mw/Mn) of the polymeric compound (A2) are the same as those of the polymeric compound (A1).

<<Positive Resist Composition>>

The polymeric compound (A1) is preferable as the component (A) of a positive resist composition including a resin component (A) which exhibits increased alkali solubility under action of acid (hereafter, referred to as "component (A)") and an acid-generator component (B) which generates acid upon irradiation (hereafter, referred to as "component (B)").

In the positive resist composition, when acid is generated from the component (B) upon exposure, the generated acid acts on the component (A) to increase the alkali solubility thereof. Therefore, in the formation of a resist pattern, by conducting selective exposure of a resist film obtained by using the positive resist composition, the exposed portions become alkali soluble, whereas the unexposed portions remain alkali insoluble, and hence, a resist pattern can be formed by alkali developing.

<Component (A)>

In the polymeric compound (A1), when acid is generated from the component (B), the —C($R^1$)($R^2$)($R^3$) group within the structural unit (a1) is dissociated. The —C($R^1$)($R^2$)($R^3$) group functions as a dissolution inhibiting group to suppress the increase in the alkali solubility of the polymeric compound (A1). By the dissociation of the dissolution inhibiting group, the alkali solubility of the polymeric compound (A1) is increased.

In the component (A), as the polymeric compound (A1), one type of compound may be used alone, or two or more types of compounds may be used in combination.

The amount of the polymeric compound (A1) within the component (A), based on the total weight of the component (A) is preferably 50 to 100% by weight, more preferably 80 to 100% by weight, and may be even 100% by weight.

The component (A) may contain a "resin that exhibits increased alkali solubility by action of acid" other than the polymeric compound (A1), as long as the effects of the present invention are not impaired.

As such a resin, there is no particular limitation, and multitude of conventional base resins of chemically amplified positive resist compositions for ArF excimer lasers or KrF excimer lasers (and particularly for ArF excimer lasers) can be appropriately selected for use.

As the "resin that exhibits increased alkali solubility by action of acid", one type of resin may be used alone, or two or more types of resins may be used in combination.

The polymeric compound (A2) of the present invention is also preferable as the component (A) of a resist composition including the component (A) and the component (B).

The polymeric compound (A2) is preferably used in combination with a conventional base resin for a chemically amplified positive resist composition. The amount of the polymeric compound (A2) within the component (A), based on the total weight of the component (A) is preferably 0.1 to 20% by weight, more preferably 0.5 to 15.0% by weight, still more preferably 1.0 to 5.0% by weight, and most preferably 2.5 to 5.0% by weight.

As the base resin to be used in combination with the polymeric compound (A2), the aforementioned "resin that exhibits increased alkali solubility by action of acid" can be used. It is particularly desirable to use the polymeric compound (A2) in combination with a copolymer (A1') including a structural unit (a1') derived from an acrylate ester containing an acid dissociable, dissolution inhibiting group. Here, the structural unit (a1') is the same as the structural unit (a1') described above in the explanation of "other structural units" for the polymeric compound (A1).

It is preferable that the copolymer (A1') further includes a structural unit (a2) derived from an acrylate ester containing a lactone-containing cyclic group.

Further, the copolymer (A1') may include a structural unit (a3) derived from an acrylate ester containing a polar group-containing aliphatic hydrocarbon group, as well as the structural unit (a1'), or the structural unit (a1') and the structural unit (a2). Furthermore, the copolymer (A1') may also include a structural unit (a4) derived from an acrylate ester containing a non-acid-dissociable aliphatic polycyclic group.

The structural units (a2), (a3) and (a4) are respectively the same as the structural units (a2), (a3) and (a4) described above in connection with the polymeric compound (A1).

As a preferable example of the copolymer (A1') to be used in combination with the polymeric compound (A2), a copolymer represented by general formula (A'-1-1) shown below can be given (wherein R is as defined for R in general formula (I) above).

The copolymer (A1') can be produced, for example, by a conventional radical polymerization or the like of the monomers corresponding with each of the structural units, using a radical polymerization initiator such as 2,2'-azobisisobutyronitrile (AIBN).

[Chemical Formula 35.]

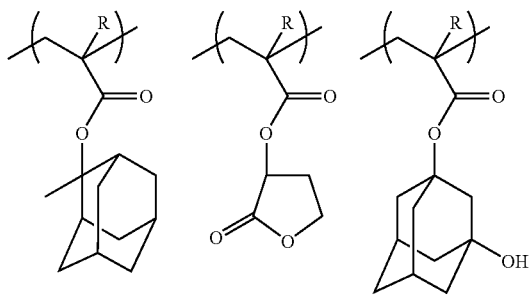

(A'-1-1)

In the formula above, R is as defined for R in general formula (I).

<Component (B)>

As the component (B), there is no particular limitation, and any of the known acid generators used in conventional chemically amplified resist compositions can be used.

Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

As an onium salt-based acid generator, for example, a compound represented by general formula (b-0) shown below can be used.

[Chemical Formula 36.]

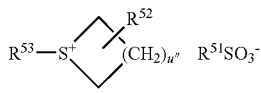

(b-0)

In the formula above, $R^{51}$ represents a linear, branched or cyclic alkyl group, or a linear, branched or cyclic fluorinated alkyl group; $R^{52}$ represents a hydrogen atom, a hydroxyl group, a halogen atom, a linear or branched alkyl group, a linear or branched halogenated alkyl group, or a linear or branched alkoxy group; $R^{53}$ represents an aryl group which may have a substituent; and u" represents an integer of 1 to 3.

In general formula (b-0), $R^{51}$ represents a linear, branched or cyclic alkyl group, or a linear, branched or cyclic fluorinated alkyl group.

The linear or branched alkyl group preferably has 1 to 10 carbon atoms, more preferably 1 to 8 carbon atoms, and most preferably 1 to 4 carbon atoms.

The cyclic alkyl group preferably has 4 to 12 carbon atoms, more preferably 5 to 10 carbon atoms, and most preferably 6 to 10 carbon atoms.

The fluorinated alkyl group preferably has 1 to 10 carbon atoms, more preferably 1 to 8 carbon atoms, and most preferably 1 to 4 carbon atoms. The fluorination ratio of the fluorinated alkyl group (percentage of the number of fluorine atoms substituting the hydrogen atoms, based on the total number of all hydrogen atoms within the alkyl group) is preferably from 10 to 100%, more preferably from 50 to 100%, and it is particularly desirable that all of the hydrogen atoms are substituted with fluorine atoms, as the acid strength increases.

$R^{51}$ is most preferably a linear alkyl group or a fluorinated alkyl group.

$R^{52}$ represents a hydrogen atom, a hydroxyl group, a halogen atom, a linear or branched alkyl group, a linear or branched halogenated alkyl group, or a linear or branched alkoxy group.

Examples of the halogen atom for $R^{52}$ include a fluorine atom, a bromine atom, a chlorine atom and an iodine atom, and a fluorine atom is preferable.

The alkyl group for $R^{52}$ is linear or branched, and preferably has 1 to 5 carbon atoms, more preferably 1 to 4 carbon atoms, and most preferably 1 to 3 carbon atoms.

The halogenated alkyl group for $R^{52}$ is a group in which a part or all of the hydrogen atoms of the alkyl group have been substituted with halogen atoms. As the alkyl group of the halogenated alkyl group, the same alkyl group for $R^{52}$ may be used. As the halogen atoms for substituting the hydrogen atoms of the alkyl group, the same halogen atom for $R^{52}$ may be used. In the halogenated alkyl group, it is preferable that 50 to 100% of the hydrogen atoms of the alkyl group be substituted with halogen atoms, and it is more preferable that all of the hydrogen atoms be substituted with halogen atoms.

The alkoxy group for $R^{52}$ is linear or branched, and preferably has 1 to 5 carbon atoms, more preferably 1 to 4 carbon atoms, and most preferably 1 to 3 carbon atoms.

Among these, as $R^{52}$, a hydrogen atom is particularly desirable.

$R^{53}$ represents an aryl group which may have a substituent, preferably an aryl group of 6 to 20 carbon atoms, and examples of the basic ring excluding the substituent include a naphthyl group, a phenyl group and an anthracenyl group. In terms of the effects of the present invention and absorption of exposure rays such as ArF excimer laser, a phenyl group is preferable.

Examples of the substituent include a hydroxyl group and a lower alkyl group (linear or branched, and preferably has no more than 5 carbon atoms, and a methyl group is particularly desirable).

As the aryl group for $R^{53}$, those which do not have a substituent are preferable.

u" is an integer of 1 to 3, preferably 2 or 3, and it is particularly desirable that u" be 3.

As preferable examples of acid generators represented by general formula (b-0), the following can be used.

[Chemical Formula 37.]

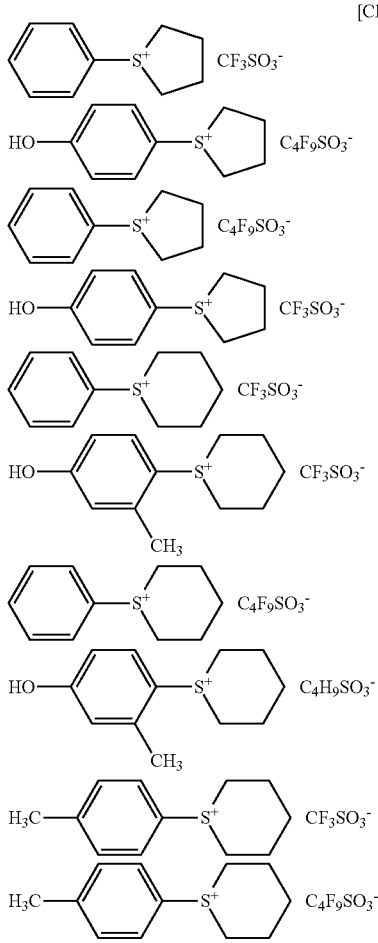

As an onium salt-based acid generator other than those represented by general formula (b-0), a compound represented by general formula (b-1) or (b-2) shown below can be used.

[Chemical Formula 38.]

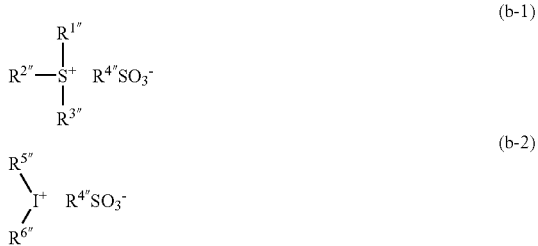

In the formula above, $R^{1\prime\prime}$ to $R^{3\prime\prime}$, $R^{5\prime\prime}$ and $R^{6\prime\prime}$ each independently represents an aryl group or alkyl group; and $R^{4\prime\prime}$ represents a linear, branched or cyclic alkyl group or fluorinated alkyl group, with the provision that at least one of $R^{1\prime\prime}$ to $R^{3\prime\prime}$ represents an aryl group, and at least one of $R^{5\prime\prime}$ and $R^{6\prime\prime}$ represents an aryl group.

In formula (b-1), $R^{1\prime\prime}$ to $R^{3\prime\prime}$ each independently represents an aryl group or an alkyl group. Further, among $R^{1\prime\prime}$ to $R^{3\prime\prime}$, at least one group represents an aryl group. Among $R^{1\prime\prime}$ to $R^{3\prime\prime}$, two or more groups are preferably aryl groups, and it is particularly desirable that all of $R^{1\prime\prime}$ to $R^{3\prime\prime}$ are aryl groups.

The aryl group for $R^{1\prime\prime}$ to $R^{3\prime\prime}$ is not particularly limited. For example, an aryl group having 6 to 20 carbon atoms may be used in which a part or all of the hydrogen atoms of the aryl group may or may not be substituted with alkyl groups, alkoxy groups, or halogen atoms.

The aryl group is preferably an aryl group having 6 to 10 carbon atoms because it can be synthesized at a low cost. Specific examples thereof include a phenyl group and naphthyl group.

The alkyl group, with which hydrogen atoms of the aryl group may be substituted, is preferably an alkyl group having 1 to 5 carbon atoms, and most preferably a methyl group, an ethyl group, a propyl group, an n-butyl group, or a tert-butyl group.

The alkoxy group, with which hydrogen atoms of the aryl group may be substituted, is preferably an alkoxy group having 1 to 5 carbon atoms, and most preferably a methoxy group or an ethoxy group.

The halogen atom, with which hydrogen atoms of the aryl group may be substituted, is preferably a fluorine atom.

The alkyl group for $R^{1\prime\prime}$ to $R^{3\prime\prime}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

It is preferable that each of $R^{1\prime\prime}$ to $R^{3\prime\prime}$ is a phenyl group or a naphthyl group, and it is particularly desirable that one of $R^{1\prime\prime}$ to $R^{3\prime\prime}$ is a phenyl group, and the other two are naphthyl groups.

$R^{4\prime\prime}$ represents a linear, branched or cyclic alkyl group or a fluorinated alkyl group.

The linear or branched alkyl group preferably has 1 to 10 carbon atoms, more preferably 1 to 8 carbon atoms, and most preferably 1 to 4 carbon atoms.

The cyclic alkyl group is preferably a cyclic group, as described for $R^{1\prime\prime}$, having 4 to 15 carbon atoms, more preferably 4 to 10 carbon atoms, and most preferably 6 to 10 carbon atoms.

The fluorinated alkyl group preferably has 1 to 10 carbon atoms, more preferably 1 to 8 carbon atoms, and most preferably 1 to 4 carbon atoms. Further, the fluorination ratio of the fluorinated alkyl group (percentage of fluorine atoms within the alkyl group) is preferably from 10 to 100%, more preferably from 50 to 100%, and it is particularly desirable that all hydrogen atoms be substituted with fluorine atoms because the acid strength increases.

$R^{4\prime\prime}$ is most preferably a linear or cyclic alkyl group or a fluorinated alkyl group.

In formula (b-2), $R^{5\prime\prime}$ and $R^{6\prime\prime}$ each independently represents an aryl group or an alkyl group. At least one of $R^{5\prime\prime}$ and $R^{6\prime\prime}$ represents an aryl group. It is preferable that both of $R^{5\prime\prime}$ and $R^{6\prime\prime}$ represent an aryl group.

As the aryl group for $R^{5\prime\prime}$ and $R^{6\prime\prime}$, the same aryl groups as those for $R^{1\prime\prime}$ to $R^{3\prime\prime}$ can be used.

As the alkyl group for $R^{5\prime\prime}$ and $R^{6\prime\prime}$, the same alkyl groups as those for $R^{1\prime\prime}$ to $R^{3\prime\prime}$ can be used.

It is particularly desirable that both of $R^{5\prime\prime}$ and $R^{6\prime\prime}$ represents a phenyl group.

As $R^{4\prime\prime}$ in formula (b-2), the same $R^{4\prime\prime}$ as those mentioned above for $R^{4\prime\prime}$ in formula (b-1) can be used.

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethylphenylsulfonium trifluoromethanesulfonate, heptafluoropropanesulfonate or nonafluorobutanesulfonate; methyldiphenylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; and di(1-naphthyl)phenylsulfonium trifluoromethanesulfonate, heptafluoropropanesulfonate or nonafluorobutanesulfonate. It is also possible to use onium salts in which the anion moiety of these onium salts are replaced by methanesulfonate, n-propanesulfonate, n-butanesulfonate, or n-octanesulfonate.

Further, onium salt-based acid generators in which the anion moiety in general formula (b-1) or (b-2) is replaced by an anion moiety represented by general formula (b-3) or (b-4) shown below (the cation moiety is the same cation as (b-1) or (b-2)) may also be used.

[Chemical Formula 39.]

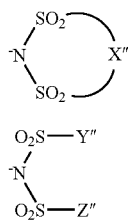

In the formula above, X" represents an alkylene group of 2 to 6 carbon atoms in which at least one hydrogen atom has been substituted with a fluorine atom; and Y" and Z" each independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Y" and Z" each independently represents a linear or branched alkyl group in which at least one hydrogen atom has been substituted with a fluorine atom, and the alkyl group has 1 to 10 carbon atoms, preferably 1 to 7 carbon atoms, and more preferably 1 to 3 carbon atoms.

The smaller the number of carbon atoms of the alkylene group for X" or those of the alkyl group for Y" and Z" within the above-mentioned range of the number of carbon atoms, the more preferable since the solubility in a resist solvent is improved.

Further, in the alkylene group for X" or the alkyl group for Y" and Z", it is preferable that the number of hydrogen atoms substituted with fluorine atoms is as large as possible because the acid strength increases and the transparency to high energy radiation of 200 nm or less or electron beam is improved. The percentage of the fluorine atoms within the alkylene group or alkyl group, i.e., the fluorination ratio is preferably from 70 to 100%, more preferably from 90 to 100%, and it is particularly desirable that the alkylene group or alkyl group be a perfluoroalkylene or perfluoroalkyl group in which all hydrogen atoms are substituted with fluorine atoms.

In the present description, an oximesulfonate-based acid generator is a compound having at least one group represented by general formula (B-1) shown below, and has a feature of generating acid by irradiation. Such oximesulfonate-based acid generators are widely used for a chemically amplified resist composition, and can be appropriately selected.

[Chemical Formula 40.]

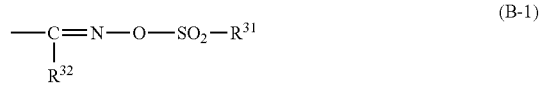

In the formula above, $R^{31}$ and $R^{32}$ each independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The expression "having a substituent" means that a part or all of the hydrogen atoms of the alkyl group or the aryl group are substituted with substituents.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which a part of the hydrogen atoms are substituted with halogen atoms, and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which a part of the hydrogen atoms are substituted with halogen atoms, and the "completely halogenated aryl group" refers to an aryl group in which all hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. Examples of the alkyl group and the aryl group for $R^{32}$ are the same as those of the alkyl group and the aryl group for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate-based acid generator include compounds represented by general formula (B-2) or (B-3) shown below.

[Chemical Formula 41.]

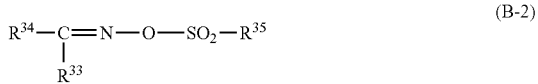

(B-2)

In the formula above, $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 42.]

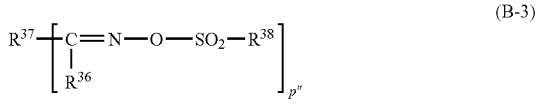

(B-3)

In the formula above, $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and still more preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthracenyl group, and a phenanthryl group, and heteroaryl groups in which a part of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. The halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, a fluorinated alkyl group is more preferable, and a partially fluorinated alkyl group is particularly desirable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), the alkyl group having no substituent and the halogenated alkyl group for $R^{36}$ are the same as the alkyl group having no substituent and the halogenated alkyl group for $R^{33}$ in general formula (B-2).

Examples of the divalent or trivalent aromatic hydrocarbon group for $R^{37}$ include groups in which one or two hydrogen atoms have been removed from the aryl group for $R^{34}$ in general formula (B-2).

As the alkyl group having no substituent or the halogenated alkyl group for $R^{38}$, the same one as the alkyl group having no substituent or the halogenated alkyl group for $R^{35}$ in general formula (B-2) can be used.

p" is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p- methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 85) may be preferably used.

Furthermore, as preferable examples, the following can be used.

[Chemical Formula 43.]

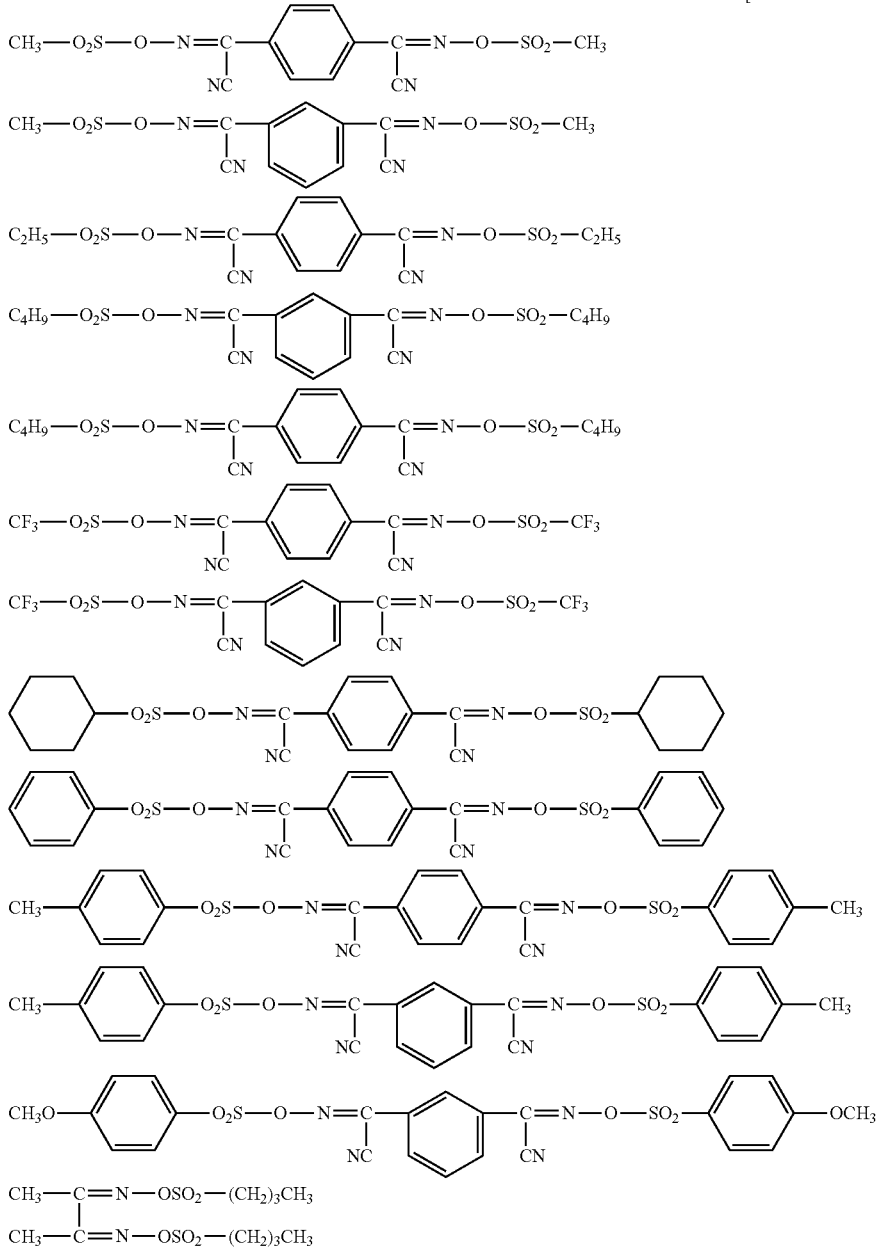

[Chemical Formula 44.]

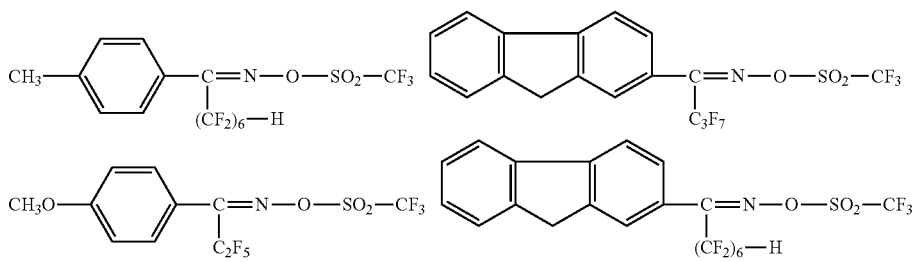

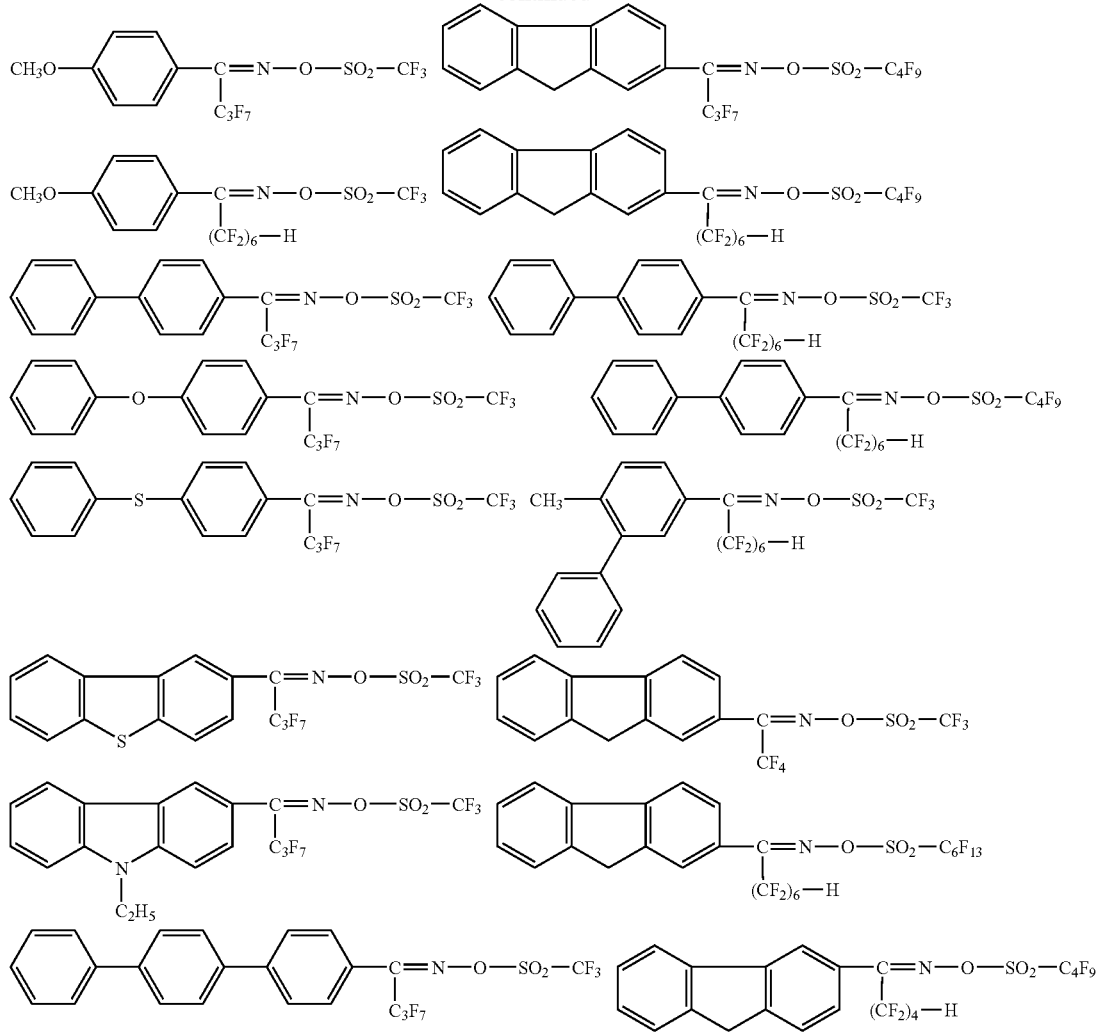

Among the above-mentioned compounds, the following 4 compounds are preferable.

[Chemical Formula 45.]

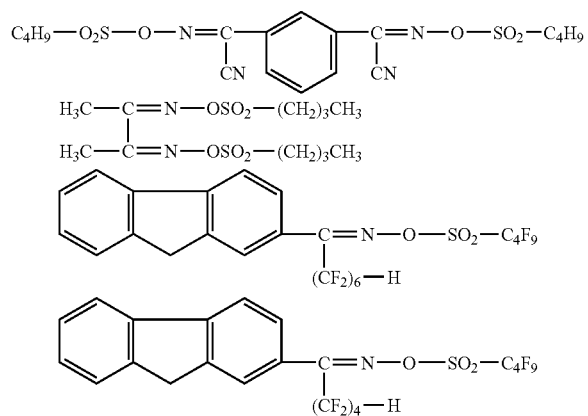

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be used.

As the component (B), one type of these acid generators may be used alone, or two or more types may be used in combination.

In the present invention, among the above-mentioned examples, as the component (B), it is preferable to use an onium salt-based acid generator having a fluorinated alkylsulfonate ion as the anion moiety and/or a diazomethane-based acid generator.

The amount of the component (B) within the positive resist composition, relative to 100 parts by weight of the component (A) is preferably 0.5 to 30 parts by weight, and more preferably 1 to 10 parts by weight. When the amount of the component (B) is within the above-mentioned range, formation of a resist pattern can be satisfactorily performed. Further, by virtue of the above-mentioned range, a uniform solution can be obtained and the storage stability becomes satisfactory.

<Optional Component>

It is preferable that the positive resist composition containing the polymeric compound of the present invention, for improving the resist pattern shape and the post exposure stability of the latent image formed by the pattern-wise exposure of the resist layer, further contains a nitrogen-containing organic compound (D) (hereafter referred to as the component (D)) as an optional component.

A multitude of these components (D) have already been proposed, and any of these known compounds may be used, although a cyclic amine, an aliphatic amine, and particularly a secondary aliphatic amine or tertiary aliphatic amine is preferable. Here, an aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkyl alcohol amines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine. Among these, alkylalcoholamines and/or trialkylamines are preferable, and alkylalcoholamines are particularly desirable. Among alkylalcoholamines, triethanolamine and triisopropanolamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

These compounds can be used either alone, or in combinations of two or more different compounds.

The component (D) is typically used in an amount within a range from 0.01 to 5.0 parts by weight, relative to 100 parts by weight of the component (A).

Furthermore, in the positive resist composition, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added as an optional component.

Examples of suitable organic carboxylic acids include acetic acid, malonic acid, citric acid, malic acid, succinic acid, benzoic acid, and salicylic acid. Among these, salicylic acid is particularly preferable.

Examples of phosphorus oxo acids or derivatives thereof include phosphoric acid, phosphonic acid and phosphinic acid. Among these, phosphonic acid is particularly desirable.

Examples of phosphorus oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

Of these, one type may be used alone, or two or more types may be used in combination.

The component (E) is typically used in an amount within a range from 0.01 to 5.0 parts by weight, relative to 100 parts by weight of the component (A).

[Component (O)]

If desired, other miscible additives can also be added to the positive resist composition. Examples of such miscible additives include additive resins for improving the performance of the resist film, dissolution inhibitors, plasticizers, stabilizers, colorants, halation prevention agents, dyes, and surfactants.

<Organic Solvent>

The positive resist composition containing the polymeric compound of the present invention can be prepared by dissolving the materials for the resist composition in an organic solvent (hereafter, frequently referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples thereof include lactones such as γ-butyrolactone; ketones such as acetone, methyl ethyl ketone, cyclohexanone, methyl-n-amyl ketone, methyl isoamyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, amylbenzene, isopropylbenzene, toluene, xylene, cymene and mesitylene.

These solvents can be used individually, or in combination as a mixed solvent.

Among these, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) used is not particularly limited, and is appropriately adjusted to a concentration which enables coating of a coating solution to a substrate, depending on the thickness of the coating film. In general, the component (S) is used in an amount such that the solid content of the resist composition is within the range from 2 to 20% by weight, and preferably from 3 to 15% by weight.

The aforementioned positive resist composition is a novel composition that was essentially unknown in the art.

In the positive resist composition, since the structural unit (a1) contains a fluorine atom, a resist film formed using the positive resist composition exhibits high hydrophobicity, as compared to the case where a fluorine atom is not contained. Therefore, the positive resist composition can be preferably used in immersion exposure described below. Further, the positive resist composition exhibits excellent lithography properties such as sensitivity, resolution, etching resistance and the like. For example, by using the positive resist composition, an extremely fine line and space pattern (L/S pattern) having a line width of no more than 120 nm can be formed. Further, the positive resist composition exhibits excellent etching resistance especially when the positive resist composition contains an aliphatic cyclic group. The etching resistance is particularly good when the aliphatic cyclic group is a polycyclic group.

As described above, the positive resist composition containing the polymeric compound of the present invention exhibits various excellent properties. In particular, as the positive resist composition exhibits high hydrophobicity, the positive resist composition can be preferably used for immersion exposure.

As described above, immersion exposure is a method in which exposure (immersion exposure) is conducted in a state where the region between the lens and the resist layer formed on a wafer (which was conventionally filled with air or an inert gas such as nitrogen) is filled with a solvent (a immersion medium) that has a larger refractive index than the refractive index of air.

In immersion exposure, when the resist film comes into contact with the immersion medium, elution of a substance within the resist film (component (B), component (D), and the like) into the immersion medium occurs. This elution of a substance causes phenomenon such as degeneration of the resist film and change in the refractive index of the immersion medium, thereby adversely affecting the lithography properties. The amount of the eluted substance is affected by the properties of the resist film surface (e.g., hydrophilicity, hydrophobicity, and the like). Therefore, it is presumed that the amount of eluted substance can be reduced by enhancing the hydrophobicity of the resist film surface.

With respect to a resist film formed using the positive resist composition containing the polymeric compound of the present invention, since the structural unit (a1) contains a fluorine atom, the hydrophobicity is enhanced, as compared to the case where a conventional positive resist composition is used. As a result, the contact angles against water, such as the static contact angle (the contact angle between the surface of a water droplet on the resist film in a horizontal state and the resist film surface), the dynamic contact angle (the contact angle at which a water droplet starts to slide when the resist film is inclined, including the contact angle at the front-end point of the water droplet in the sliding direction (advancing angle) and the contact angle at the rear-end point of the water droplet in the sliding direction (receding angle)) and sliding angle (the inclination angle of the resin film at which a water droplet starts to slide when the resist film is inclined) are changed. For example, the higher the hydrophobicity of the resist film, the larger the static contact angle and the dynamic contact angle, and the smaller the sliding angle.

Therefore, by the positive resist composition containing the polymeric compound of the present invention, elution of a substance can be suppressed during immersion exposure.

As shown in FIG. 1, when a droplet 1 is placed on a plane 2 and the plane 2 is gradually inclined, the advancing angle is the angle $\theta_1$ formed between the lower end 1*a* of the droplet 1 and the plane 2 as the droplet 1 starts to move (slide) on the plane 2. Further, at this time (when the droplet 1 starts to move (slide) on the plane 2), the receding angle is the angle $\theta_2$ formed between the upper end 1*b* of the droplet 1 and the plane 2, and the sliding angle is the inclination angle $\theta_3$ of the plane 2.

In the present description, the static contact angle and the dynamic contact angle are measured in the following manner.

First, a resist composition solution is spin-coated onto a silicon substrate, and then heated under predetermined conditions, e.g., at 110 to 115° C. for 90 seconds, to form a resist film.

Subsequently, the contact angles can be measured using commercially available measurement apparatuses such as DROP MASTER-700 (product name; manufactured by Kyowa Interface Science Co. Ltd.), AUTO SLIDING ANGLE: SA-30 DM (product name; manufactured by Kyowa Interface Science Co. Ltd.), and AUTO DISPENSER: AD-31 (product name; manufactured by Kyowa Interface Science Co. Ltd.).

With respect to a resist film formed using the positive resist composition containing the polymeric compound of the present invention, it is preferable that the receding angle be 55 degrees (°) or more, more preferably 55 to 150°, still more preferably 55 to 130°, and most preferably 60 to 100°. When the receding angle is at least as large as 55°, the hydrophobicity of the resist film becomes excellent, and the effect of suppressing the elution of a substance during immersion exposure is enhanced. On the other hand, when the receding angle is no more than 150°, the lithography properties become excellent.

For the same reasons as described above, with respect to a resist film formed using the positive resist composition containing the polymeric compound of the present invention, it is preferable that the static contact angle be 70° or more, more preferably 70 to 100°, and most preferably 80 to 95°.

The level of the static contact angle, the receding angle and the like can be adjusted by the formulation of the resist composition, for example, the type of the component (A), and the amount of the structural unit (a1) within the component (A). For example, by increasing the amount of the structural unit (a1) within the component (A), the hydrophobicity of the obtained resist composition can be enhanced, and the static contact angle and the receding angle become large.

As described above, by the positive resist composition, elution of a substance into the immersion medium can be suppressed. Therefore, by using the positive resist composition in immersion exposure, degeneration of the resist film and change in refractive index of the immersion medium can also be suppressed. Further, as a result of suppression of change in refractive index of the immersion medium and the like, a resist pattern having an excellent shape can be formed.

Furthermore, the level of staining of the lens within the exposure apparatus can be reduced. Therefore, there is no need for protection against these disadvantages, and hence, the present invention can contribute to simplifying the process and the exposure apparatus.

Moreover, as described above, when immersion exposure is performed using a scanning-type immersion exposure apparatus as disclosed in Non-Patent Document 1, tracking ability of water with respect to the movement of the lens (water tracking ability) is required. By using the positive resist composition, a resist film exhibiting high hydrophobicity and high water tracking ability can be formed. In addition, the positive resist composition exhibits excellent lithography properties, and hence, when the positive resist composition is used as a resist in immersion exposure, a resist pattern can be formed without any practical problems.

As described above, the positive resist composition containing the polymeric compound of the present invention exhibits not only excellent lithography properties that are generally required (e.g., sensitivity, resolution, etching resistance and the like), but also properties required for resist materials in immersion exposure (e.g., hydrophobicity, suppression of substance elution, water tracking ability, and the like). Therefore, the positive resist composition can be preferably used for immersion exposure.

<<Method of Forming a Resist Pattern>>

Next, the method of forming a resist pattern will be described.

The method of forming a resist pattern according to the present embodiment includes: applying a resist composition containing the polymeric compound of the present invention to a substrate to form a resist film on the substrate; conducting exposure of the resist film; and developing the resist film to form a resist pattern.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) can be used.

The method of forming a resist pattern according to the present invention can be performed, for example, as follows.

Firstly, the positive resist composition is applied onto a substrate such as a silicon wafer using a spinner or the like, and a prebake (post applied bake (PAB)) is conducted under temperature conditions of 80 to 150° C. for 40 to 120 seconds, preferably 60 to 90 seconds to form a resist film. Then, using a predetermined exposure source, the resist film is selectively exposed through or not through a desired mask pattern. That is, the resist film is either exposed through a mask pattern, or directly irradiated with an electron beam to form a pattern.

After the selective exposure, post exposure bake (PEB) is conducted under temperature conditions of 80 to 150° C. for 40 to 120 seconds, preferably 60 to 90 seconds. Subsequently, developing is conducted using an alkali developing solution such as a 0.1 to 10% by weight aqueous solution of tetramethylammonium hydroxide (TMAH), preferably followed by rinsing with pure water. The rinsing can be conducted, for example, by dropping or spraying water onto the surface of the substrate while rotating the substrate, thereby washing off the developing solution and resist composition for immersion exposure dissolved in the developing solution from the substrate. Finally, drying is conducted, thereby obtaining a resist pattern.

An organic or inorganic antireflection film may be provided between the substrate and the coated layer of the resist composition.

The wavelength to be used for exposure is not particularly limited, and the exposure can be conducted using radiations such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present invention is particularly effective to ArF excimer laser.

<Immersion Exposure>

As described above, the positive resist composition containing the polymeric compound of the present invention can be preferably used for immersion exposure.

In an immersion exposure, a resist pattern can be formed by conducting immersion exposure in the step of subjecting the resist film to exposure in the aforementioned method of forming a resist pattern. That is, a pattern can be formed by conducting a step of subjecting the resist film to immersion exposure.

The step of conducting immersion exposure can be conducted, for example, as follows.

Firstly, the region between the resist film and the lens at the lowermost point of the exposure apparatus is pre-filled with a solvent (immersion medium) that has a larger refractive index than the refractive index of air, and then, exposure (immersion exposure) is conducted in this state through or not through a desired mask pattern.

The wavelength to be used for exposure is not particularly limited, and any of those described above can be used.

The immersion medium preferably exhibits a refractive index larger than the refractive index of air but smaller than the refractive index of the resist film formed from the positive resist composition. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids and silicon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

The positive resist composition is particularly resistant to any adverse effects caused by water, and because the resulting sensitivity and shape of the resist pattern are excellent, water is preferably used as the immersion medium which exhibits a refractive index that is larger than the refractive index of air. Furthermore, water is also preferred in terms of cost, safety, environmental friendliness, and versatility.

EXAMPLES

The following is a description of examples of the present invention, although the scope of the present invention is by no way limited by these examples.

Example 1

Synthesis of Monomer

Synthesis of 7,7,7-trifluoro-3-ethyl-3-heptanol 1.3 g of magnesium, 10.0 g of 1-bromo-4,4,4-trifluorobutane and 20 g of tetrahydrofuran were charged into a four-necked flask equipped with a nitrogen feeding tube, a reflux condenser, a dropping funnel and a thermometer, and a Grignard reagent was prepared by a conventional method. Then, a mixture of 5.0 g of 3-pentanone and 4 g of tetrahydrofuran was dropwise added to the obtained Grignard reagent at a temperature of 25 to 35° C. over 30 minutes, followed by stirring at the same temperature for 1 hour. The reaction mixture was treated by a conventional method, and the resulting organic phase was washed with water, followed by drying with anhydrous magnesium sulfate. Thereafter, the resultant was concentrated under reduced pressure, thereby obtaining 7.9 g of 7,7,7-trifluoro-3-ethyl-3-heptanol in the form of a pale yellow oily matter.

Synthesis of 7,7,7-trifluoro-3-ethyl-3-heptyl methacrylate 7.9 g of 7,7,7-trifluoro-3-ethyl-3-heptanol obtained above, 0.2 g of 4-dimethylaminopyridine, 7.1 g of triethylamine and 10 g of acetonitrile were charged into a four-necked flask equipped with a stirrer, a thermometer and a dropping funnel, and were dissolved by stirring.

Subsequently, 6.7 g of methacrylic acid chloride was dropwise added to the resulting solution at about 75° C. over 30 minutes, followed by stirring at the same temperature for 2 hours. Then, the reaction mixture was cooled to room temperature, and washing was conducted once with a mixture of 8.8 g of potassium carbonate and 100 ml of water, and once with a 10% saline solution. Thereafter, the resultant was dried with anhydrous magnesium sulfate, and then concentrated under reduced pressure. The obtained concentrate was purified by silica gel column chromatography, thereby obtaining 5.7 g of 7,7,7-trifluoro-3-ethyl-3-heptyl methacrylate.

The $^1$H-NMR data of the obtained 7,7,7-trifluoro-3-ethyl-3-heptyl methacrylate were as follows.

$^1$H-NMR (CDCl$_3$) δ: 0.82-0.87 (tr, 6H, —CH$_3$), 1.46-1.58 (m, 2H, —CH$_2$—), 1.78-1.97 (m, 9H, =C—CH$_3$, —C—CH$_2$—), 1.98-2.16 (m, 2H, CF$_3$CH$_2$—), 5.49 (s, 1H, C=CH$_2$), 6.01 (s, 1H, C=CH$_2$).

From the results above, it was confirmed that 7,7,7-trifluoro-3-ethyl-3-heptyl methacrylate had a structure represented by formula (I-1) shown below.

[Chemical Formula 46.]

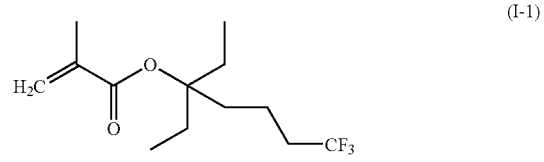

(I-1)

Example 2

Synthesis of Resin 27 g of tetrahydrofuran and 11.98 g of the 7,7,7-trifluoro-3-ethyl-3-hepthyl methacrylate obtained in Example 1 were charged into a four-necked flask equipped with a nitrogen feeding tube, a reflux condenser, a dropping funnel and a thermometer. Then, the four-necked flask was purged with nitrogen, and the temperature was elevated to 67° C. While maintaining the temperature at 67° C., a solution obtained by dissolving 0.30 g of 2,2'-azobis(2,4-dimethylvaleronitrile) in 3 g of tetrahydrofuran was dropwise added to the four-necked flask over 10 minutes. Thereafter, while maintaining the temperature at 67° C., the resultant was stirred for 6 hours, and then cooled to room temperature. The resulting polymerization reaction mixture was dropwise added to an excess amount of a methanol/water mixture, and the precipitated resin was separated by filtration, followed by washing and drying, thereby obtaining 4.0 g of an objective resin represented by chemical formula (1) shown below, in the form of a white solid. The weight average molecular weight (Mw) and dispersity (Mw/Mn) of the obtained resin were 6,500 and 1.4, respectively.

83

[Chemical Formula 47.]

(1)

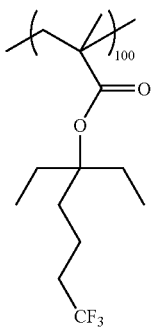

Example 3

Synthesis of Resin 30 g of tetrahydrofuran, 5.63 g of 7,7,7-trifluoro-3-ethyl-3-hepthyl methacrylate obtained in Example 1, 3.40 g of γ-butyrolactone methacrylate and 2.36 g of 3-hydroxy-1-adamantyl methacrylate were charged into a four-necked flask equipped with a nitrogen feeding tube, a reflux condenser, a dropping funnel and a thermometer. Then, the four-necked flask was purged with nitrogen, and the temperature was elevated to 67° C. While maintaining the temperature at 67° C., a solution obtained by dissolving 0.37 g of 2,2'-azobis(2,4-dimethylvaleronitrile) in 3 g of tetrahydrofuran was dropwise added to the four-necked flask over 10 minutes. Thereafter, while maintaining the temperature at 67° C., the resultant was stirred for 6 hours, and then cooled to room temperature. The resulting polymerization reaction mixture was dropwise added to an excess amount of a methanol/water mixture, and the precipitated resin was separated by filtration, followed by washing and drying, thereby obtaining 7.4 g of an objective resin in the form of a white solid. The weight average molecular weight (Mw) and dispersity (Mw/Mn) of the obtained resin were 11,200 and 1.8, respectively. Further, the compositional ratio of the obtained resin was analyzed by $^{13}$C-NMR. As a result, it was found that the copolymerization molar ratio of 7,7,7-trifluoro-3-ethyl-3-hepthyl methacrylate, γ-butyrolactone methacrylate and 3-hydroxy-1-adamantyl methacrylate was 32:44:24, and it was confirmed that the resin was represented by chemical formula (2) shown below.

[Chemical Formula 48.]

(2)

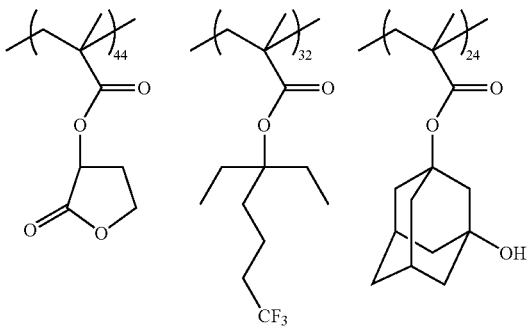

84

Comparative Example 1

Synthesis of Monomer

Synthesis of 1,1,1,3,3,3-hexafluoro-2-methyl-2-propyl methacrylate 7.3 g of 1,1,1,3,3,3-hexafluoro-2-methyl-2-propanol, 0.2 g of 4-dimethylaminopyridine, 4.9 g of triethylamine and 20 g of acetone were charged into a four-necked flask equipped with a stirrer, a thermometer and a dropping funnel, and were dissolved by stirring. Then, 4.6 g of methacrylic acid chloride was dropwise added to the resulting solution at about 5° C. over 30 minutes, followed by stirring at the same temperature for 3 hours. Thereafter, the reaction solution was washed with water, thereby obtaining 7.5 g of 1,1,1,3,3,3-hexafluoro-2-methyl-2-propyl methacrylate. The $^1$H-NMR data of the obtained 1,1,1,3,3,3-hexafluoro-2-methyl-2-propyl methacrylate were as follows.

$^1$H-NMR (CDCl$_3$) δ: 1.95 (s, 3H, =C—CH$_3$), 2.01 (s, 3H, C—CH$_3$), 5.71 (s, 1H, C=CH$_2$), 6.18 (s, 1H, C=CH$_2$).

From the results above, it was confirmed that the obtained 1,1,1,3,3,3-hexafluoro-2-methyl-2-propyl methacrylate had the structure shown below.

[Chemical Formula 49.]

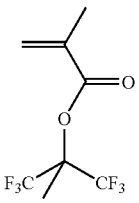

<Synthesis of Resin>

30 g of tetrahydrofuran, 5.00 g of 1,1,1,3,3,3-hexafluoro-2-methyl-2-propyl methacrylate obtained above, 3.40 g of γ-butyrolactone methacrylate and 2.36 g of 3-hydroxy-1-adamantyl methacrylate were charged into a four-necked flask equipped with a nitrogen feeding tube, a reflux condenser, a dropping funnel and a thermometer. Then, the four-necked flask was purged with nitrogen, and the temperature was elevated to 67° C. While maintaining the temperature at 67° C., a solution obtained by dissolving 0.37 g of 2,2'-azobis(2,4-dimethylvaleronitrile) in 3 g of tetrahydrofuran was dropwise added to the four-necked flask over 10 minutes. Thereafter, while maintaining the temperature at 67° C., the resultant was stirred for 6 hours, and then cooled to room temperature. The resulting polymerization reaction mixture was dropwise added to an excess amount of a methanol/water mixture, and the precipitated resin was separated by filtration, followed by washing and drying, thereby obtaining 7.0 g of an objective resin in the form of a white solid. The weight average molecular weight (Mw) and dispersity (Mw/Mn) of the obtained resin were 10,600 and 1.6, respectively. Further, the compositional ratio of the obtained resin was analyzed by $^{13}$C-NMR. As a result, it was found that the copolymerization molar ratio of 1,1,1,3,3,3-hexafluoro-2-methyl-2-propyl methacrylate, γ-butyrolactone methacrylate and 3-hydroxy-1-adamantyl methacrylate was 39:39:22, and it was confirmed that the resin was represented by chemical formula (4) shown below.

[Chemical Formula 50.]

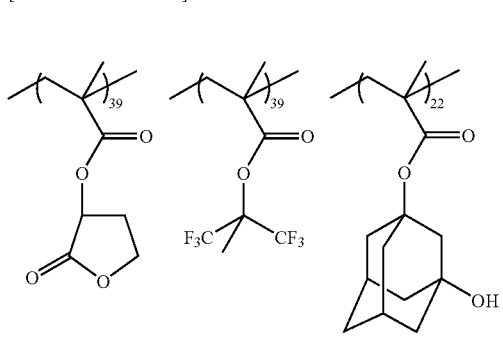
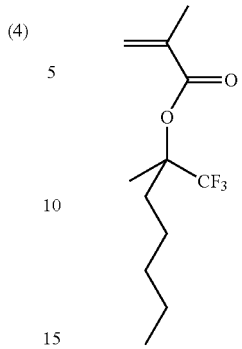

(4)

Comparative Example 2

Synthesis of Monomer

Synthesis of 1,1,1-trifluoro-2-methyl-2-heptanol 24.9 g of trimethyl(trifluoromethyl)silane, 16.0 g of 2-heptanone, 38 g of tetrahydrofuran and 350 mg of tetrabutylammonium fluoride trihydrate were charged into a four-necked flask equipped with a nitrogen feeding tube, a reflux condenser, a dropping funnel and a thermometer, and a reaction was effected by a conventional method. Then, 17.5 g of hydrochloric acid was dropwise added to the reaction mixture at a temperature of 25 to 48° C. over 30 minutes, followed by stirring at about 48° C. for 2 hours. The reaction mixture was treated by a conventional method, and the resulting organic phase was washed with a saline solution, followed by drying with anhydrous magnesium sulfate. Thereafter, the resultant was concentrated under reduced pressure, thereby obtaining 26.4 g of 1,1,1-trifluoro-2-methyl-2-heptanol in the form of a pale brown oily matter.

Synthesis of 1,1,1-trifluoro-2-methyl-2-heptyl methacrylate 21.4 g of 1,1,1-trifluoro-2-methyl-2-heptanol obtained above, 0.6 g of 4-dimethylaminopyridine, 23.3 g of triethylamine and 35 g of acetonitrile were charged into a four-necked flask equipped with a stirrer, a thermometer and a dropping funnel, and were dissolved by stirring. Subsequently, 20.9 g of methacrylic acid chloride was dropwise added to the resulting solution at about 75° C. over 30 minutes, followed by stirring at the same temperature for 7 hours. Then, the reaction mixture was cooled to room temperature, and washing was conducted once with a mixture of 27.6 g of potassium carbonate and 300 ml of water, and once with a 10% saline solution. Thereafter, the resultant was dried with anhydrous magnesium sulfate, and then concentrated under reduced pressure. The obtained concentrate was purified by silica gel column chromatography, thereby obtaining 14.0 g of 1,1,1-trifluoro-2-methyl-2-heptyl methacrylate. The $^1$H-NMR data of the obtained 1,1,1-trifluoro-2-methyl-2-heptyl methacrylate were as follows.

$^1$H-NMR (CDCl$_3$) δ: 0.85-0.90 (tr, 3H, —CH$_3$), 1.20-1.49 (m, 6H, —CH$_2$—CH$_2$—CH$_2$—), 1.70 (s, 3H, C—CH$_3$), 1.93 (s, 3H, =C—CH$_3$), 1.96-2.26 (m, 2H, C—CH$_2$—), 5.59 (s, 1H, C=CH$_2$), 6.10 (s, 1H, C=CH$_2$).

From the results above, it was confirmed that the obtained 1,1,1-trifluoro-2-methyl-2-heptyl methacrylate had the structure shown below.

[Chemical Formula 51.]

<Synthesis of Resin>

30 g of tetrahydrofuran, 5.05 g of 1,1,1-trifluoro-2-methyl-2-heptyl methacrylate obtained above, 3.40 g of γ-butyrolactone methacrylate and 2.36 g of 3-hydroxy-1-adamantyl methacrylate were charged into a four-necked flask equipped with a nitrogen feeding tube, a reflux condenser, a dropping funnel and a thermometer. Then, the four-necked flask was purged with nitrogen, and the temperature was elevated to 67° C. While maintaining the temperature at 67° C., a solution obtained by dissolving 0.37 g of 2,2'-azobis(2,4-dimethylvaleronitrile) in 3 g of tetrahydrofuran was dropwise added to the four-necked flask over 10 minutes. Thereafter, while maintaining the temperature at 67° C., the resultant was stirred for 6 hours, and then cooled to room temperature. The resulting polymerization reaction mixture was dropwise added to an excess amount of a methanol/water mixture, and the precipitated resin was separated by filtration, followed by washing and drying, thereby obtaining 8.1 g of an objective resin in the form of a white solid. The weight average molecular weight (Mw) and dispersity (Mw/Mn) of the obtained resin were 12,800 and 2.0, respectively. Further, the compositional ratio of the obtained resin was analyzed by $^{13}$C-NMR. As a result, it was found that the copolymerization molar ratio of 1,1,1-trifluoro-2-methyl-2-heptyl methacrylate, γ-butyrolactone methacrylate and 3-hydroxy-1-adamantyl methacrylate was 37:41:22, and it was confirmed that the resin was represented by chemical formula (5) shown below.

[Chemical Formula 52.]

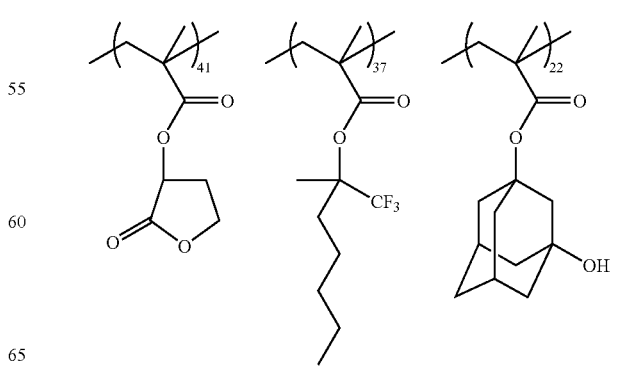

(5)

Test Examples 1 to 4

The components shown in Table 1 were mixed together and dissolved to obtain positive resist compositions.

TABLE 1

| | Component (A) | Component (B) | | Component (D) | Component (S) |
|---|---|---|---|---|---|
| Test Example 1 | (A)-2 [100] | (B)-1 [3.5] | (B)-2 [1] | (D)-1 [0.3] | (S)-1 [2000] |
| Test Example 2 | (A)-3 [100] | (B)-1 [3.5] | (B)-2 [1] | (D)-1 [0.3] | (S)-1 [2000] |
| Test Example 3 | (A)-4 [100] | (B)-1 [3.5] | (B)-2 [1] | (D)-1 [0.3] | (S)-1 [2000] |
| Test Example 4 | (A)-5 [100] | (B)-1 [3.5] | (B)-2 [1] | (D)-1 [0.3] | (S)-1 [2000] |

In Table 1, the values in brackets [ ] indicate the amount (in terms of parts by weight) of the component added. Further, the reference characters indicate the following.
- (A)-2: a resin represented by chemical formula (2) above
- (A)-3: a resin represented by chemical formula (3) shown below
- (A)-4: a resin represented by chemical formula (4) above
- (A)-5: a resin represented by chemical formula (5) above
- (B)-1: triphenylsulfonium nonafluorobutanesulfonate
- (B)-2: (4-methylphenyl)diphenylsulfonium trifluoromethanesulfonate
- (D)-1: triethanolamine
- (S)-1: a mixed solvent of PGMEA/PGME=6/4 (weight ratio)

[Chemical Formula 53.]

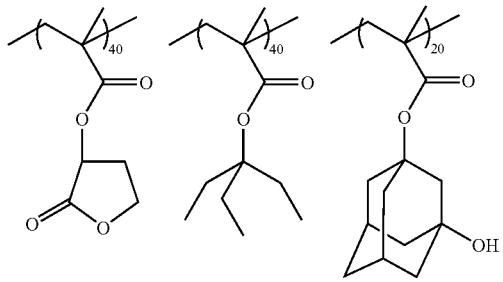

(3)

The component (A)-3 was copolymerized by a conventional dropwise polymerization method, using monomers for deriving the respective structural units. The weight average molecular weight (Mw) was 10,000, and the dispersity (Mw/Mn) was 1.8.

Using the obtained resist compositions, evaluations were conducted as follows.

<Evaluation of Hydrophobicity>

With respect to the resist compositions of Test Examples 1 and 2, the static contact angle and dynamic contact angle (receding angle) (hereafter, referred to as contact angles) of the resist film surface prior to and after exposure were measured in the following manner, to thereby evaluate the hydrophobicity of the resist film.

Each of the resist compositions of Test Examples 1 and 2 was applied onto an 8-inch silicon wafer using a spinner, and was then prebaked (PAB) on a hotplate at 110° C. for 60 seconds and dried, thereby forming a resist film having a film thickness of 150 nm.

Subsequently, 50 μl of water was dropped onto the surface of the resist film (prior to exposure), and the contact angles were measured using DROP MASTER-700 (manufactured by Kyowa Interface Science Co. Ltd.).

Further, a resist film was formed in the same manner as described above, and an open frame exposure (exposure without a mask) was performed (exposure dose: 20 mJ/cm$^2$) with an ArF excimer laser (193 nm), using an ArF exposure apparatus NSR-S-302A (manufactured by Nikon Corporation, NA (numerical aperture)=0.60, ⅔ annular illumination). Then, PEB treatment was conducted at 90° C. for 60 seconds, or at 150° C. for 60 seconds. Thereafter, the contact angles of the surface of the resist film (after exposure) were determined in the same manner as described above.

The results of the contact angles as measured with respect to the resist film prior to and after exposure are shown in Table 2. Further, the PAB/PEB temperature conditions are also indicated in Table 2.

As seen from the results, when compared under the same bake conditions, the static contact angle and dynamic contact angle (receding angle) prior to and after exposure were large in Test Example 1, as compared to those in Test Example 2. From these results, it was confirmed that the hydrophobicity of the resist film obtained using the resist composition of Test Example 1 was higher than that of the resist film obtained using the resist composition of Test Example 2.

TABLE 2

| | | Prior to exposure | | After exposure | |
|---|---|---|---|---|---|
| | PAB/PEB [° C.] | Static contact angle (°) | Dynamic contact angle (°) | Static contact angle (°) | Dynamic contact angle (°) |
| Test Example 1 | 110/90 | 86 | 63 | 62.1 | 35.6 |
| | 110/150 | 87.4 | 63.9 | 57.6 | 34.4 |
| Test Example 2 | 110/90 | 72.6 | 54.9 | 52.4 | 32.6 |
| | 110/150 | 76.8 | 57.6 | 44.2 | 34.1 |

<Evaluation of Lithography Properties>
[Resolution/Sensitivity]

Using the resist compositions of Test Examples 1 to 4, resist patterns were formed in the following manner.

An organic anti-reflection film composition (product name: ARC-29, manufactured by Brewer Science Ltd.) was applied onto an 8-inch silicon wafer using a spinner, and the composition was then baked at 205° C. for 60 seconds, thereby forming an organic anti-reflection film having a film thickness of 77 nm.

Then, each of the resist composition solutions of Test Examples 1 to 4 was applied onto the anti-reflection film using a spinner, and was then prebaked (PAB) at 90° C. for 60 seconds, thereby forming a resist film (film thickness: 150 nm).

Subsequently, the resist film was selectively irradiated with an ArF excimer laser (193 nm) through a mask pattern, using an ArF exposure apparatus NSR-S302A (manufactured by Nikon Corporation, NA (numerical aperture)=0.60, ⅔ annular illumination). Thereafter, a post exposure bake (PEB) treatment was conducted at 90° C. for 60 seconds, followed by development for 30 seconds at 23° C. in a 2.38% by weight aqueous solution of tetramethylammonium hydroxide (TMAH). Then, the resist was washed for 30 seconds with pure water, followed by drying by shaking, thereby forming a line and space (1:1) resist pattern (L/S pattern).

As a result, in the examples using the resist compositions of Test Examples 1 and 2, a L/S pattern having a line width of 120 nm (pitch: 240 nm) was formed.

Further, the optimum exposure dose (Eop) (unit: mJ/cm$^2$ (amount of energy per unit area)) for forming an L/S pattern having a line width of 120 nm and a pitch of 240 nm, i.e., sensitivity was determined. The results are shown in Table 3.

On the other hand, in the examples using the resist compositions of Test Examples 3 and 4, a resist pattern could not be resolved.

[Line Width Roughness (LWR)]

With respect to each of the L/S patterns formed with the above-mentioned Eop, line widths at 5 points in the lengthwise direction of the line were measured using a measuring scanning electron microscope (product name: S-9220, manufactured by Hitachi, Ltd.), and from the results, the value of 3 times the standard deviation s (i.e., 3s) was calculated as a yardstick of LWR. The results are shown in Table 3. It was confirmed that the 3s value of the resist composition of Test Example 1 was superior to that of the resist composition of Test Example 2. The smaller this 3s value is, the lower the level of roughness of the line width, indicating that an L/S pattern with a uniform width was obtained.

TABLE 3

|  | PAB/PEB [° C.] | Eop [mJ/cm$^2$] | LWR |
|---|---|---|---|
| Test Example 1 | 90/90 | 39.02 | 8.46 |
| Test Example 2 | 90/90 | 23.4 | 10.88 |

As seen from the results, with respect to the resist composition of Test Example 1, it was confirmed that a resist film exhibiting high hydrophobicity as compared to a conventional resist composition could be formed, LWR was reduced, and excellent lithography properties could be achieved.

Test Example 5 to 10

The components shown in Table 4 were mixed together and dissolved to obtain positive resist compositions.

TABLE 4

|  | Component (A) |  | Component (B) | Component (D) | Component (S) |
|---|---|---|---|---|---|
| Test Example 5 | (A)-6 [100] | (A)-1 [0.5] | (B)-1 [5] | (D)-1 [0.3] | (S)-1 [2000] |
| Test Example 6 | (A)-6 [100] | (A)-1 [1.0] | (B)-1 [5] | (D)-1 [0.3] | (S)-1 [2000] |
| Test Example 7 | (A)-6 [100] | (A)-1 [3.0] | (B)-1 [5] | (D)-1 [0.3] | (S)-1 [2000] |
| Test Example 8 | (A)-6 [100] | (A)-1 [5.0] | (B)-1 [5] | (D)-1 [0.3] | (S)-1 [2000] |
| Test Example 9 | (A)-6 [100] | (A)-1 [10.0] | (B)-1 [5] | (D)-1 [0.3] | (S)-1 [2000] |
| Test Example 10 | (A)-6 [100] |  | (B)-1 [5] | (D)-1 [0.3] | (S)-1 [2000] |

In Table 4, the values in brackets [ ] indicate the amount (in terms of parts by weight) of the component added. Further, the reference characters indicate the following.

(A)-6: a resin represented by chemical formula (6) shown below
(A)-1: a resin represented by chemical formula (1) above
(B)-1: triphenylsulfonium nonafluorobutanesulfonate
(D)-1: triethanolamine
(S)-1: a mixed solvent of PGMEA/PGME=6/4 (weight ratio)

[Chemical Formula 54.]

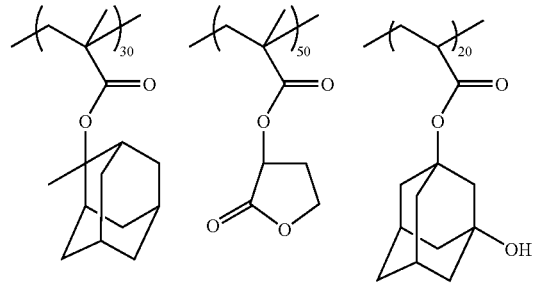

(6)

The resin (6) was copolymerized by a conventional dropwise polymerization method, using monomers for deriving the respective structural units. The weight average molecular weight (Mw) was 10,000, and the dispersity (Mw/Mn) was 1.8.

Using the obtained resist compositions, evaluations were conducted as follows.

<Evaluation of Hydrophobicity>

With respect to the resist compositions of Test Examples 5 to 10, the static contact angle and dynamic contact angle (advancing angle and receding angle) (hereafter, referred to as contact angles) of the resist film surface prior to and after exposure were measured in the following manner, to thereby evaluate the hydrophobicity of the resist film.

Each of the resist compositions of Test Examples 5 to 10 was applied onto an 8-inch silicon wafer using a spinner, and was then prebaked (PAB) on a hotplate at 115° C. for 60 seconds and dried, thereby forming a resist film having a film thickness of 150 nm.

Subsequently, 50 μl of water was dropped onto the surface of the resist film (prior to exposure), and the contact angles were measured using DROP MASTER-700 (manufactured by Kyowa Interface Science Co. Ltd.).

Further, a resist film was formed in the same manner as described above, and an open frame exposure (exposure without a mask) was performed (exposure dose: 20 mJ/cm$^2$) with an ArF excimer laser (193 nm), using an ArF exposure apparatus NSR-S-302A (manufactured by Nikon Corporation, NA (numerical aperture)=0.60, σ=0.75), and the contact angles of the surface of the resist film (after exposure) were determined in the same manner as described above.

Figure 2:
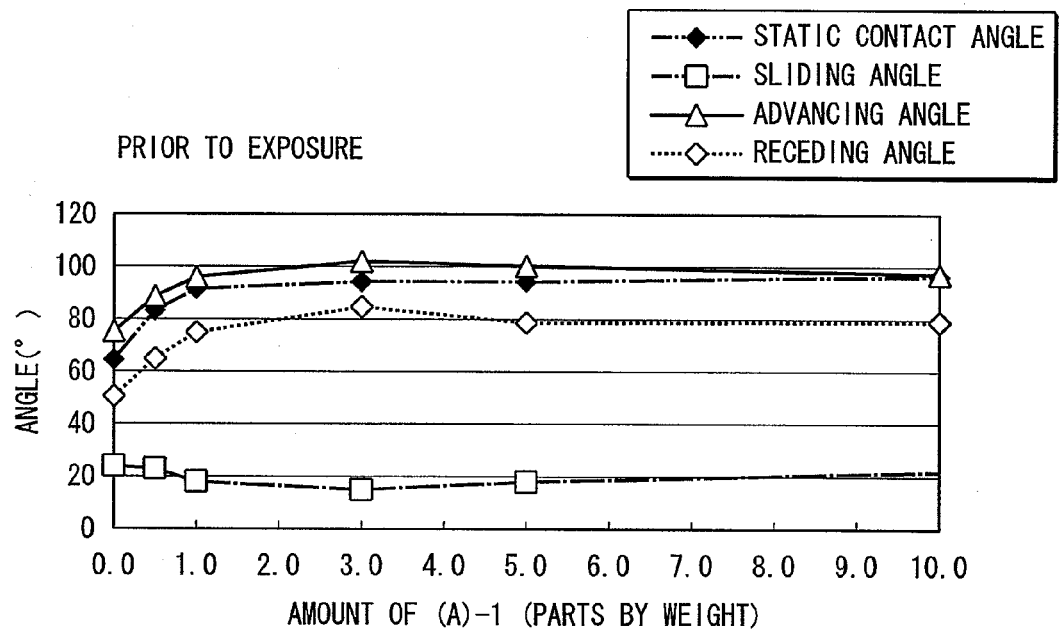
FIG. 2 is a graph showing the relationship between the amount of (A)-1 (parts by weight) and the contact angles of the resist film prior to exposure, as evaluated in Test Examples 5 to 10.
Figure 3:
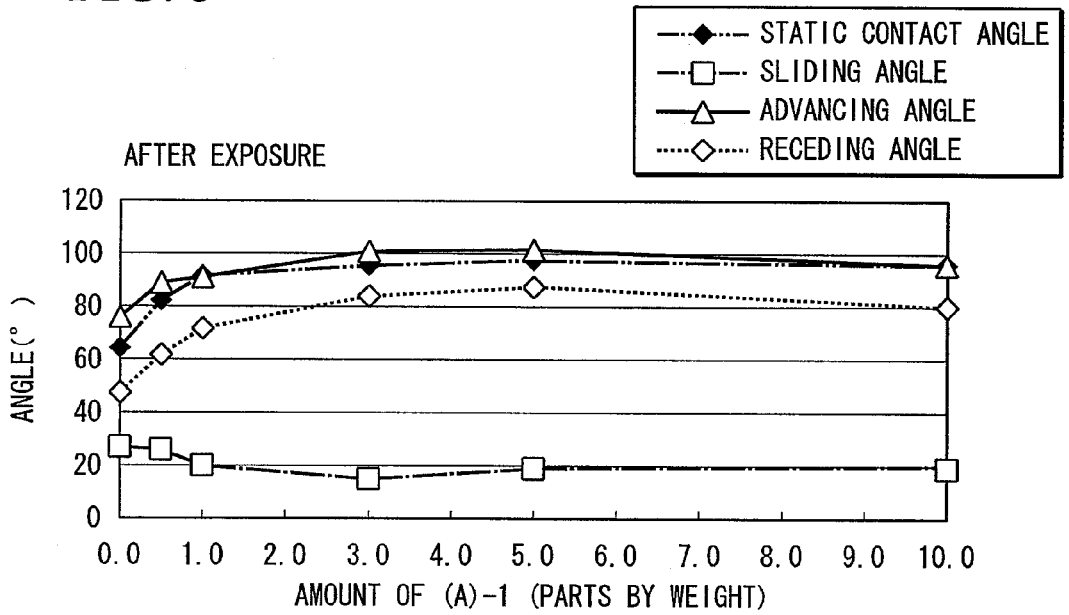
FIG. 3 is a graph showing the relationship between the amount of (A)-1 (parts by weight) and the contact angles of the resist film after exposure, as evaluated in Test Examples 5 to 10.

The results of the contact angles measured with respect to the resist film prior to and after exposure are shown in FIG. 2 and FIG. 3. FIG. 2 and FIG. 3 are graphs showing the relationship between the amount of (A)-1 (parts by weight) and the contact angles of the resist film prior to/after exposure, as evaluated in Test Examples 5 to 10.

As seen from the results, it was confirmed that the resist films formed using the resist compositions of Test Examples 5 to 9 in which the component (A)-1 was added exhibited high hydrophobicity.

<Evaluation of Lithography Properties>
[Resolution/Sensitivity]

Using the resist compositions of Test Examples 5 to 10, resist patterns were formed in the following manner.

An organic anti-reflection film composition (product name: ARC-29A, manufactured by Brewer Science Ltd.) was applied onto an 8-inch silicon wafer using a spinner, and the composition was then baked at 205° C. for 60 seconds, thereby forming an organic anti-reflection film having a film thickness of 77 nm. Then, each of the resist composition solutions of Test Examples 5 to 10 was applied onto the anti-reflection film using a spinner, and was then prebaked (PAB) on a hotplate at 115° C. for 60 seconds and dried, thereby forming a resist film having a film thickness of 150 nm.

Subsequently, the resist film was selectively irradiated with an ArF excimer laser (193 nm) through a mask pattern, using an ArF exposure apparatus NSR-S302A (manufactured by Nikon Corporation, NA (numerical aperture)=0.60, ⅔ annular illumination). Thereafter, a post exposure bake (PEB) treatment was conducted at 115° C. for 60 seconds, followed by development for 30 seconds at 23° C. in a 2.38% by weight aqueous solution of tetramethylammonium hydroxide. Then, the resist was washed for 30 seconds with pure water, followed by drying by shaking, thereby forming a line and space (1:1) resist pattern (L/S pattern) having a line width of 120 nm.

Further, the optimum exposure dose (Eop) (unit: mJ/cm$^2$ (amount of energy per unit area)) for forming an L/S pattern having a line width of 120 nm and a pitch of 240 nm, i.e., sensitivity was determined. As a result, it was found that the optimum exposure dose was 17.8 for Test Example 5, 17.8 for Test Example 6, 16.2 for Test Example 7, 16.2 for Test Example 8, 14.6 for Test Example 9, and 17 for Test Example 10. Thus, it was found that the level of sensitivity in Test Examples 5 to 9 was about the same or higher than that in Test Example 10.

[Line Width Roughness (LWR)]

With respect to each of the L/S patterns formed with the above-mentioned Eop, line widths at 5 points in the lengthwise direction of the line were measured using a measuring scanning electron microscope (product name: S-9220, manufactured by Hitachi, Ltd.; acceleration voltage: 800V), and from the results, the value of 3 times the standard deviation s (i.e., 3s) was calculated as a yardstick of LWR. As a result, it was found that the 3s values were almost the same in all examples. The smaller this 3s value is, the lower the level of roughness of the line width, indicating that an L/S pattern with a uniform width was obtained. The LWR values for the resist compositions of Test Examples 5 to 10 were about 12 to 13 nm, and were almost the same.

[Mask Error Factor (MEF)]

With the above-mentioned Eop, L/S patterns were formed using a mask pattern targeting an L/S pattern having a line width of 130 nm and a pitch of 260 nm and a mask pattern targeting an L/S pattern having a line width of 120 nm and a pitch of 260 nm. With respect to the formed L/S patterns, the MEF was determined by the following formula.

$$\text{MEF} = |CD_{130} - CD_{120}| / |MD_{130} - MD_{120}|$$

In this formula, $CD_{130}$ and $CD_{120}$ represent the respective line widths (nm) of the actual L/S patterns respectively formed using the mask pattern targeting a line width of 130 nm and the mask pattern targeting a line width of 120 nm, and $MD_{130}$ and $MD_{120}$ represent the respective target line widths (nm), meaning $MD_{130}$=130 and $MD_{120}$=120. The MEF is a parameter that indicates how faithfully mask patterns of differing line width or hole diameter can be reproduced using the same exposure dose (namely, the mask reproducibility). The closer the MEF value is to 1, the better the mask reproducibility of the resist pattern formed.

As a result, it was found that in the examples using the resist compositions of Test Examples 5 to 9, the MEF values were closer to 1, as compared to that in the example using the resist composition of Test Example 10.

As seen from the results above, it was found that the resist compositions of Test Examples 5 to 9 showed the same level of performance as that of the resist composition of Test Example 10 for various lithography properties. Especially, in the example using the resist composition of Test Example 7, it was confirmed that the amount of residue at exposed portions was smallest, and the change in the characteristics of the film was smallest. Thus, it was confirmed that the most preferable amount of (A)-1 relative to 100 parts by weight of (A)-6 was 3 parts by weight. From these results, it was confirmed that the resist compositions of Test Examples 5 to 9 were capable of forming resist films with high hydrophobicity, and exhibited excellent lithography properties.

Test Examples 11 to 13

The components shown in Table 5 were mixed together and dissolved to obtain positive resist compositions.

TABLE 5

|  | Component (A) | | Component (B) | Component (D) | Component (E) | Component (O) | Component (S) | |
| --- | --- | --- | --- | --- | --- | --- | --- | --- |
| Test Example 11 | (A)-7 [100] | (A)-1 [0.5] | (B)-3 [8] | (D)-2 [1.2] | (E)-1 [1.32] | (O)-1 [0.1] | (S)-1 [2000] | (S)-3 [10] |
| Test Example 12 | (A)-7 [100] | (A)-1 [1.0] | (B)-3 [8] | (D)-2 [1.2] | (E)-1 [1.32] | (O)-1 [0.1] | (S)-1 [2000] | (S)-3 [10] |
| Test Example 13 | (A)-7 [100] | | (B)-3 [8] | (D)-2 [1.2] | (E)-1 [1.32] | (O)-1 [0.1] | (S)-1 [2000] | (S)-3 [10] |

In Table 5, the values in brackets [ ] indicate the amount (in terms of parts by weight) of the component added. Further, the reference characters indicate the following.

(A)-1: a resin represented by chemical formula (1) above (A)-7: a resin represented by chemical formula (7) shown below (B)-3: (4-methylphenyl)diphenylsulfonium nonafluorobutanesulfonate (D)-2: tri-n-pentylamine (E)-1: salicylic acid (O)-1: a surfactant (product name: XR104, manufactured by Dainippon Ink and Chemicals, Inc.)

(S)-1: a mixed solvent of PGMEA/PGME=6/4 (weight ratio)

(S)-3: γ-butyrolactone

[Chemical Formula 55.]

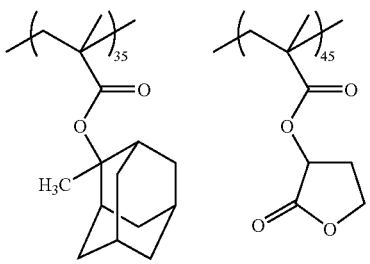

(7)

-continued

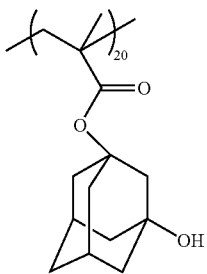

The resin (7) was copolymerized by a conventional dropwise polymerization method, using monomers for deriving the respective structural units. The weight average molecular weight (Mw) was 7,000, and the dispersity (Mw/Mn) was 1.5.

<Evaluation of Eluted Substance>

Using the resist compositions of Test Examples 11 to 13, resist films were formed in the same manner as in the examples using the resist compositions of Test Examples 5 to 10.

Then, using VRC310S (product name; manufactured by S.E.S CO., LTD.), one droplet of pure water (50 µl) was moved from the center of the wafer in a circular manner at room temperature at a constant linear velocity (total area of the resist film that came in contact with the droplet: 221.56 cm$^2$).

Thereafter, the droplet was collected, and analyzed by an analyzing apparatus Agilent-HP1100 LC-MSD (product name; manufactured by Agilent Technologies), and the total amount of elution ($\times 10^{-12}$ mol/cm$^2$) of the cation moiety (PAG+) and anion moiety (PAG−) of the component (B), the component (D) and the component (E) was determined. The results are shown in Table 6.

Further, resist films were formed in the same manner as described above, and an open frame exposure (exposure without a mask) was performed (exposure dose: 20 mJ/cm$^2$) with an ArF excimer laser (193 nm) using an ArF exposure apparatus NSR-S302A (manufactured by Nikon Corporation, NA (numerical aperture)=0.60, ⅔ annular illumination).

Subsequently, each of the exposed resist films were analyzed in the same manner as described above to thereby determine the total amount of elution ($\times 10^{-12}$ mol/cm$^2$) of the cation moiety (PAG+) and anion moiety (PAG−) of the component (B), the component (D) and the component (E). The results are shown in Table 6.

TABLE 6

| | Amount of elution (× 10−12 mol/cm$^2$) | | | | | | | | |
|---|---|---|---|---|---|---|---|---|---|
| | Prior to exposure | | | | After exposure | | | | |
| | Component (B) | | Component | Component | Component (B) | | Component | Component | |
| | PAG+ | PAG− | (D) | (E) | PAG+ | PAG− | (D) | (E) | Total |
| Test Example 11 | 5.83 | 6.77 | 0.95 | 0.84 | 0.01 | 22.39 | 0.03 | 6.82 | 43.64 |
| Test Example 12 | 1.65 | 1.93 | 0.00 | 0.68 | 0.00 | 8.25 | 0.00 | 4.39 | 16.91 |
| Test Example 13 | 24.16 | 31.26 | 13.89 | 2.48 | 0.64 | 52.63 | 6.21 | 10.72 | 141.98 |

As seen from the results shown in Table 6, in Test Examples 11 and 12, the total amount of elution of the components (B), (D) and (E) to the immersion medium (water) prior to and after exposure was small. Therefore, it was confirmed that the effect of suppressing elution of a substance during immersion exposure was high in Test Examples 11 and 12.

INDUSTRIAL APPLICABILITY

According to the present invention, there are provided a novel compound, and a polymeric compound including the compound as a monomer unit, which can be preferably used as a component of a positive resist composition. A positive resist composition containing the polymeric compound of the present invention exhibits not only excellent lithography properties (sensitivity, resolution, etching resistance, and the like) that are generally required, but also excellent properties required for immersion resist materials in immersion exposure (hydrophobicity, capability of suppressing elution of a substance, water tracking ability, and the like). Thus, the positive resist composition is preferable for immersion exposure. Therefore, the present invention is extremely useful in industry.

The invention claimed is:

1. A compound represented by general formula (I) shown below:

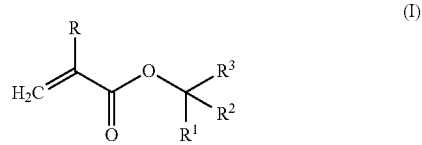

(I)

wherein R represents a hydrogen atom, a halogen atom, a lower alkyl group or a halogenated lower alkyl group; each of $R^1$ to $R^3$ independently represents a linear or branched alkyl group or a linear fluorinated alkyl group, with the provision that no fluorine atom is bonded to a carbon atom adjacent to the tertiary carbon atom to which $R^1$ to $R^3$ are bonded, and at least one of $R^1$ to $R^3$ represents a fluorinated alkyl group; and $R^2$ and $R^3$ may form a ring structure.

2. The compound according to claim 1, wherein the linear fluorinated alkyl group is a 4,4,4-trifluoro-n-butyl group.

3. A polymeric compound comprising a structural unit (a1) represented by general formula (II) shown below:

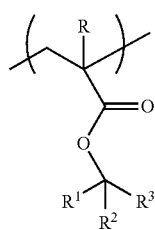

(II)

wherein R represents a hydrogen atom, a halogen atom, a lower alkyl group or a halogenated lower alkyl group; each of $R^1$ to $R^3$ independently represents a linear or branched alkyl group or a linear fluorinated alkyl group, with the provision that no fluorine atom is bonded to a carbon atom adjacent to the tertiary carbon atom to which $R^1$ to $R^3$ are bonded, and at least one of $R^1$ to $R^3$ represents a fluorinated alkyl group; and $R^2$ and $R^3$ may form a ring structure.

4. The polymeric compound according to claim 3, which further comprises a structural unit (a2) derived from an acrylate ester containing a lactone-containing cyclic group.

5. The polymeric compound according to claim 3 or 4, which further comprises a structural unit (a3) derived from an acrylate ester containing a polar group-containing aliphatic hydrocarbon group.

6. The polymeric compound according to claim 3, wherein the —C($R^1$)($R^2$)($R^3$) group in general formula (II) is an acid dissociable group.

7. The compound according to claim 3, wherein the linear fluorinated alkyl group is a 4,4,4-trifluoro-n-butyl group.

\* \* \* \* \*